(12) United States Patent
Matsuda et al.

(10) Patent No.: US 8,538,104 B2
(45) Date of Patent: Sep. 17, 2013

(54) METHOD OF ANALYZING MOTION OF IMAGING TARGET BY MEANS OF TAGGED MR IMAGES, AND MRI DEVICE

(75) Inventors: Tetsuya Matsuda, Kyoto (JP); Akira Amano, Kyoto (JP)

(73) Assignee: Kyoto University, Kyoto (JP)

( * ) Notice: Subject to any disclaimer, the term of this patent is extended or adjusted under 35 U.S.C. 154(b) by 136 days.

(21) Appl. No.: 13/266,244

(22) PCT Filed: Jan. 8, 2010

(86) PCT No.: PCT/JP2010/050173
§ 371 (c)(1), (2), (4) Date: Oct. 26, 2011

(87) PCT Pub. No.: WO2010/125832
PCT Pub. Date: Nov. 4, 2010

(65) Prior Publication Data
US 2012/0045107 A1 Feb. 23, 2012

(30) Foreign Application Priority Data
Apr. 30, 2009 (JP) .................................. 2009-111371

(51) Int. Cl.
*G06K 9/00* (2006.01)
*A61B 5/05* (2006.01)

(52) U.S. Cl.
USPC .......................... 382/128; 382/274; 600/410

(58) Field of Classification Search
USPC ................. 382/100, 103, 106–107, 128–134, 382/154, 162, 168, 173, 181, 194, 199, 232, 382/254, 274, 276, 305, 312; 600/410, 413; 324/309, 306; 378/4, 21, 23
See application file for complete search history.

(56) References Cited

U.S. PATENT DOCUMENTS

| | | | |
|---|---|---|---|
| 6,546,274 B2* | 4/2003 | Itagaki et al. | 600/413 |
| 6,892,089 B1* | 5/2005 | Prince et al. | 600/410 |
| 7,545,141 B2* | 6/2009 | Kimura | 324/306 |
| 2008/0015428 A1* | 1/2008 | Epstein et al. | 600/410 |
| 2011/0080170 A1* | 4/2011 | Miyazaki | 324/309 |

FOREIGN PATENT DOCUMENTS
JP 2007-190114 8/2007

OTHER PUBLICATIONS

Yu Shimizu et al., "Shinzo 3-jigen MRI . . . Tag Kosaten Kenshutsuho" Dai 26 Kai Japanese Society of Medical Imaging Technology Taikai Shoroku-shu (CD ROM), 2007 A1-2.
Elias A. Zerhouni et al., "Human Heart: Tagging with MR Imaging . . . Myocardial Motion" Radiology, 169, 59-63 Oct. 1988.
Albert Montillo et al., "Extracting Tissue . . . Gabor filter banks," SPIE vol. 5369, Bellingham, WA, 2004.
Keiko Maehara et al., "Improving Tag . . . Coded Tagging MRI" IEICE Technical Report MI2008-173 (Jan. 2009) Copyright, 2009.

* cited by examiner

*Primary Examiner* — Seyed Azarian
(74) *Attorney, Agent, or Firm* — Clark & Brody

(57) ABSTRACT

A method for analyzing motion of an imaging target by means of tagged MR images includes performing, on the same motion of an imaging target, $N_L$ ($N_L$: positive integer not less than 2) times of cine imaging by means of different tag patterns, to obtain $N_L$ pieces of time-series tagged MR images taken for a plurality of time phases in the motion of the imaging target, arranging $N_L$ pieces of pixel values of the same pixel in the $N_L$ pieces of tagged MR images at each time phase into a pixel value sequence having a length $N_L$ for the corresponding pixel, and analyzing the motion of the imaging target in the time-series tagged MR images by detecting pixels whose pixel value sequences constitute the same code sequence in different time phases. Each of the tag patterns is formed such that the pixel value sequence constitutes a predetermined code sequence.

16 Claims, 29 Drawing Sheets

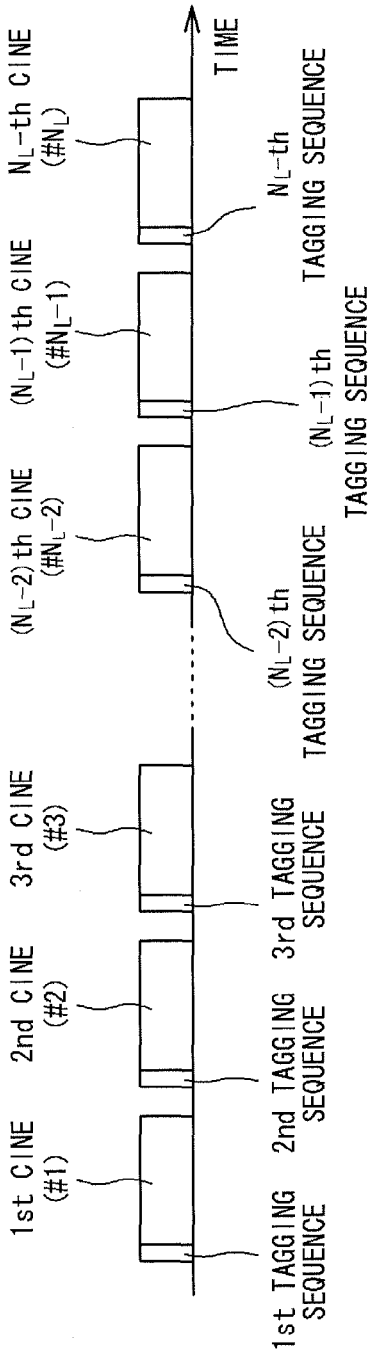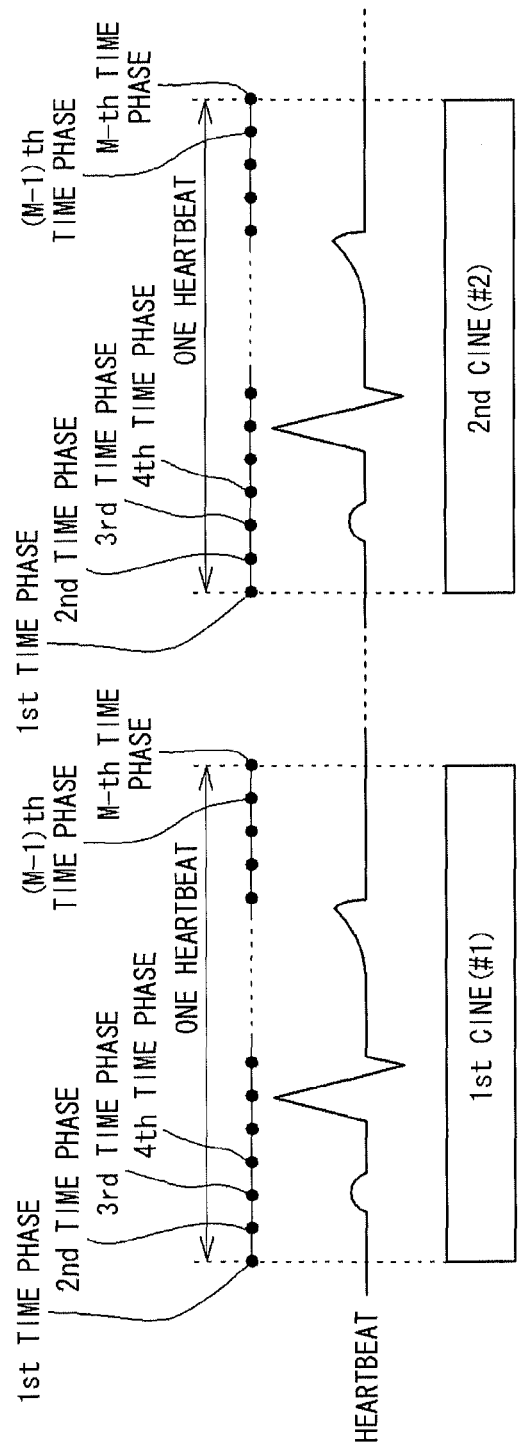
FIG. 5(a)
FIG. 5(b)

FIG. 9
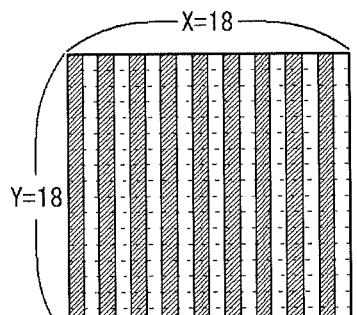
1st TAG PATTERN
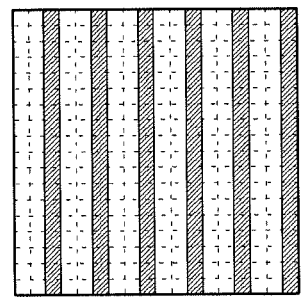
2nd TAG PATTERN
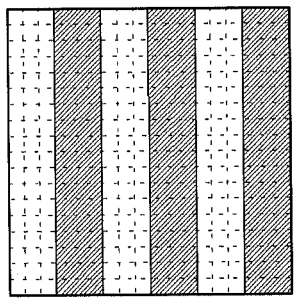
3rd TAG PATTERN
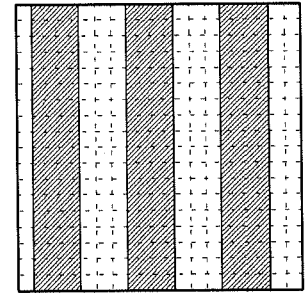
4th TAG PATTERN
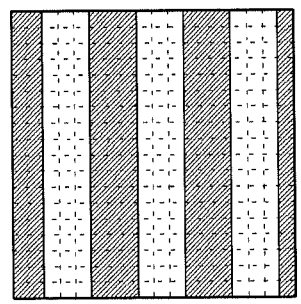
5th TAG PATTERN
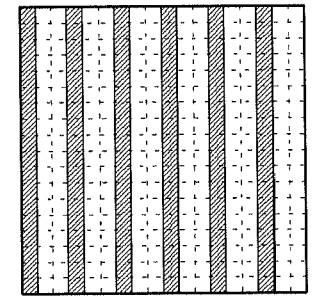
6th TAG PATTERN
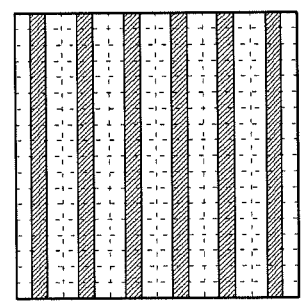
7th TAG PATTERN

*FIG. 10*

| | X=18 | | | | | | | | | | | | | | | | |
|---|---|---|---|---|---|---|---|---|---|---|---|---|---|---|---|---|---|
| $L_6$ | $L_5$ | $L_4$ | $L_3$ | $L_2$ | $L_1$ | $L_6$ | $L_5$ | $L_4$ | $L_3$ | $L_2$ | $L_1$ | $L_6$ | $L_5$ | $L_4$ | $L_3$ | $L_2$ | $L_1$ |
| $L_6$ | $L_5$ | $L_4$ | $L_3$ | $L_2$ | $L_1$ | $L_6$ | $L_5$ | $L_4$ | $L_3$ | $L_2$ | $L_1$ | $L_6$ | $L_5$ | $L_4$ | $L_3$ | $L_2$ | $L_1$ |
| $L_6$ | $L_5$ | $L_4$ | $L_3$ | $L_2$ | $L_1$ | $L_6$ | $L_5$ | $L_4$ | $L_3$ | $L_2$ | $L_1$ | $L_6$ | $L_5$ | $L_4$ | $L_3$ | $L_2$ | $L_1$ |
| $L_6$ | $L_5$ | $L_4$ | $L_3$ | $L_2$ | $L_1$ | $L_6$ | $L_5$ | $L_4$ | $L_3$ | $L_2$ | $L_1$ | $L_6$ | $L_5$ | $L_4$ | $L_3$ | $L_2$ | $L_1$ |
| $L_6$ | $L_5$ | $L_4$ | $L_3$ | $L_2$ | $L_1$ | $L_6$ | $L_5$ | $L_4$ | $L_3$ | $L_2$ | $L_1$ | $L_6$ | $L_5$ | $L_4$ | $L_3$ | $L_2$ | $L_1$ |
| $L_6$ | $L_5$ | $L_4$ | $L_3$ | $L_2$ | $L_1$ | $L_6$ | $L_5$ | $L_4$ | $L_3$ | $L_2$ | $L_1$ | $L_6$ | $L_5$ | $L_4$ | $L_3$ | $L_2$ | $L_1$ |
| $L_6$ | $L_5$ | $L_4$ | $L_3$ | $L_2$ | $L_1$ | $L_6$ | $L_5$ | $L_4$ | $L_3$ | $L_2$ | $L_1$ | $L_6$ | $L_5$ | $L_4$ | $L_3$ | $L_2$ | $L_1$ |
| $L_6$ | $L_5$ | $L_4$ | $L_3$ | $L_2$ | $L_1$ | $L_6$ | $L_5$ | $L_4$ | $L_3$ | $L_2$ | $L_1$ | $L_6$ | $L_5$ | $L_4$ | $L_3$ | $L_2$ | $L_1$ |
| $L_6$ | $L_5$ | $L_4$ | $L_3$ | $L_2$ | $L_1$ | $L_6$ | $L_5$ | $L_4$ | $L_3$ | $L_2$ | $L_1$ | $L_6$ | $L_5$ | $L_4$ | $L_3$ | $L_2$ | $L_1$ |
| $L_6$ | $L_5$ | $L_4$ | $L_3$ | $L_2$ | $L_1$ | $L_6$ | $L_5$ | $L_4$ | $L_3$ | $L_2$ | $L_1$ | $L_6$ | $L_5$ | $L_4$ | $L_3$ | $L_2$ | $L_1$ |
| $L_6$ | $L_5$ | $L_4$ | $L_3$ | $L_2$ | $L_1$ | $L_6$ | $L_5$ | $L_4$ | $L_3$ | $L_2$ | $L_1$ | $L_6$ | $L_5$ | $L_4$ | $L_3$ | $L_2$ | $L_1$ |
| $L_6$ | $L_5$ | $L_4$ | $L_3$ | $L_2$ | $L_1$ | $L_6$ | $L_5$ | $L_4$ | $L_3$ | $L_2$ | $L_1$ | $L_6$ | $L_5$ | $L_4$ | $L_3$ | $L_2$ | $L_1$ |
| $L_6$ | $L_5$ | $L_4$ | $L_3$ | $L_2$ | $L_1$ | $L_6$ | $L_5$ | $L_4$ | $L_3$ | $L_2$ | $L_1$ | $L_6$ | $L_5$ | $L_4$ | $L_3$ | $L_2$ | $L_1$ |
| $L_6$ | $L_5$ | $L_4$ | $L_3$ | $L_2$ | $L_1$ | $L_6$ | $L_5$ | $L_4$ | $L_3$ | $L_2$ | $L_1$ | $L_6$ | $L_5$ | $L_4$ | $L_3$ | $L_2$ | $L_1$ |
| $L_6$ | $L_5$ | $L_4$ | $L_3$ | $L_2$ | $L_1$ | $L_6$ | $L_5$ | $L_4$ | $L_3$ | $L_2$ | $L_1$ | $L_6$ | $L_5$ | $L_4$ | $L_3$ | $L_2$ | $L_1$ |
| $L_6$ | $L_5$ | $L_4$ | $L_3$ | $L_2$ | $L_1$ | $L_6$ | $L_5$ | $L_4$ | $L_3$ | $L_2$ | $L_1$ | $L_6$ | $L_5$ | $L_4$ | $L_3$ | $L_2$ | $L_1$ |
| $L_6$ | $L_5$ | $L_4$ | $L_3$ | $L_2$ | $L_1$ | $L_6$ | $L_5$ | $L_4$ | $L_3$ | $L_2$ | $L_1$ | $L_6$ | $L_5$ | $L_4$ | $L_3$ | $L_2$ | $L_1$ |
| $L_6$ | $L_5$ | $L_4$ | $L_3$ | $L_2$ | $L_1$ | $L_6$ | $L_5$ | $L_4$ | $L_3$ | $L_2$ | $L_1$ | $L_6$ | $L_5$ | $L_4$ | $L_3$ | $L_2$ | $L_1$ |

Y=18

3 mm WIDTH TAGGED IMAGE 1 mm WIDTH TAGGED IMAGE

M SEQUENCE DETERMINATION RESULT

1st TIME PHASE (SHIFT BY 0.25 PIXEL TO LEFT)

FIG. 14(a)
ACTUAL POSITION OF IMAGING TARGET

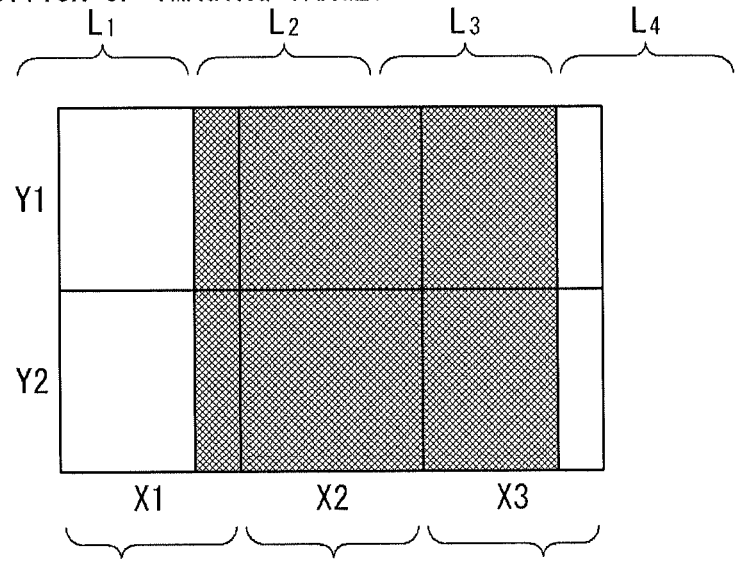

CORRELATION WITH $L_1$ = 0.75  CORRELATION WITH $L_1$ = 0  CORRELATION WITH $L_1$ = 0
CORRELATION WITH $L_2$ = 0.25  CORRELATION WITH $L_2$ = 0.75  CORRELATION WITH $L_2$ = 0
CORRELATION WITH $L_3$ = 0  CORRELATION WITH $L_3$ = 0.25  CORRELATION WITH $L_3$ = 0.75
CORRELATION WITH $L_4$ = 0  CORRELATION WITH $L_4$ = 0  CORRELATION WITH $L_4$ = 0.25
CORRELATION WITH $L_5$ = 0  CORRELATION WITH $L_5$ = 0  CORRELATION WITH $L_5$ = 0
CORRELATION WITH $L_6$ = 0  CORRELATION WITH $L_6$ = 0  CORRELATION WITH $L_6$ = 0

FIG. 14(b)
PIXEL VALUES IN IMAGING TARGET

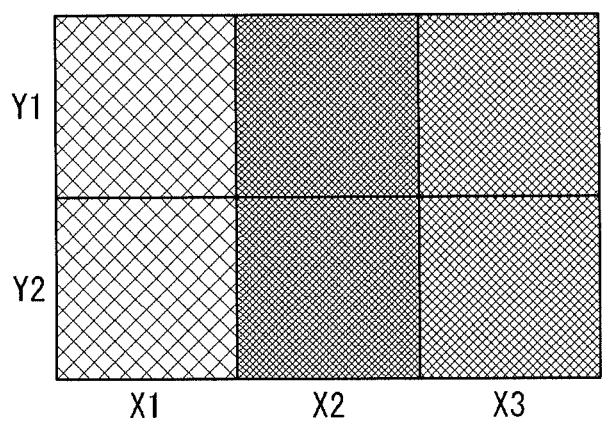

2nd TIME PHASE (SHIFT BY 0.5 PIXEL TO LEFT)

FIG. 15(a)
ACTUAL POSITION OF IMAGING TARGET

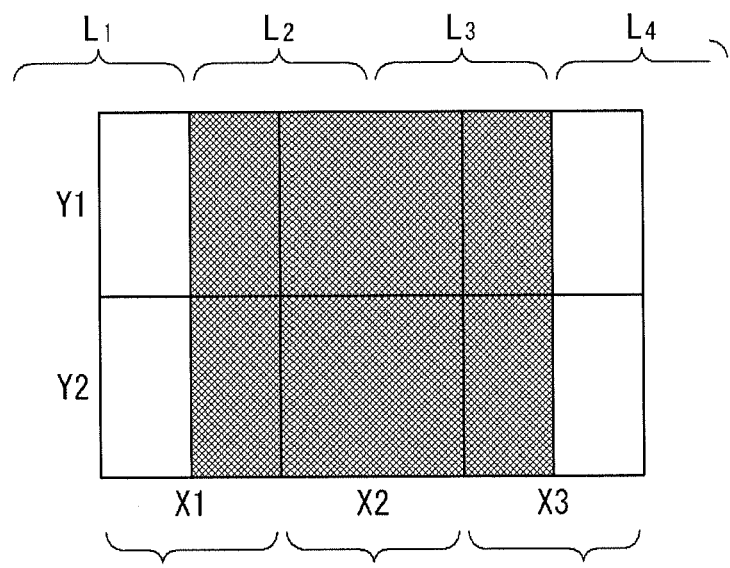

| CORRELATION WITH $L_1$ = 0.5 | CORRELATION WITH $L_1$ = 0 | CORRELATION WITH $L_1$ = 0 |
| CORRELATION WITH $L_2$ = 0.5 | CORRELATION WITH $L_2$ = 0.5 | CORRELATION WITH $L_2$ = 0 |
| CORRELATION WITH $L_3$ = 0 | CORRELATION WITH $L_3$ = 0.5 | CORRELATION WITH $L_3$ = 0.5 |
| CORRELATION WITH $L_4$ = 0 | CORRELATION WITH $L_4$ = 0 | CORRELATION WITH $L_4$ = 0.5 |
| CORRELATION WITH $L_5$ = 0 | CORRELATION WITH $L_5$ = 0 | CORRELATION WITH $L_5$ = 0 |
| CORRELATION WITH $L_6$ = 0 | CORRELATION WITH $L_6$ = 0 | CORRELATION WITH $L_6$ = 0 |

FIG. 15(b)
PIXEL VALUES IN IMAGING TARGET

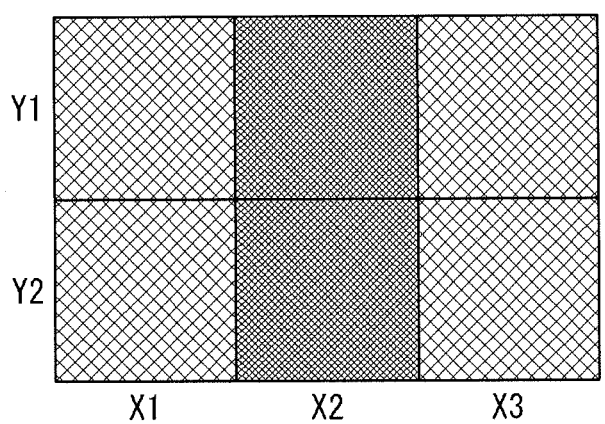

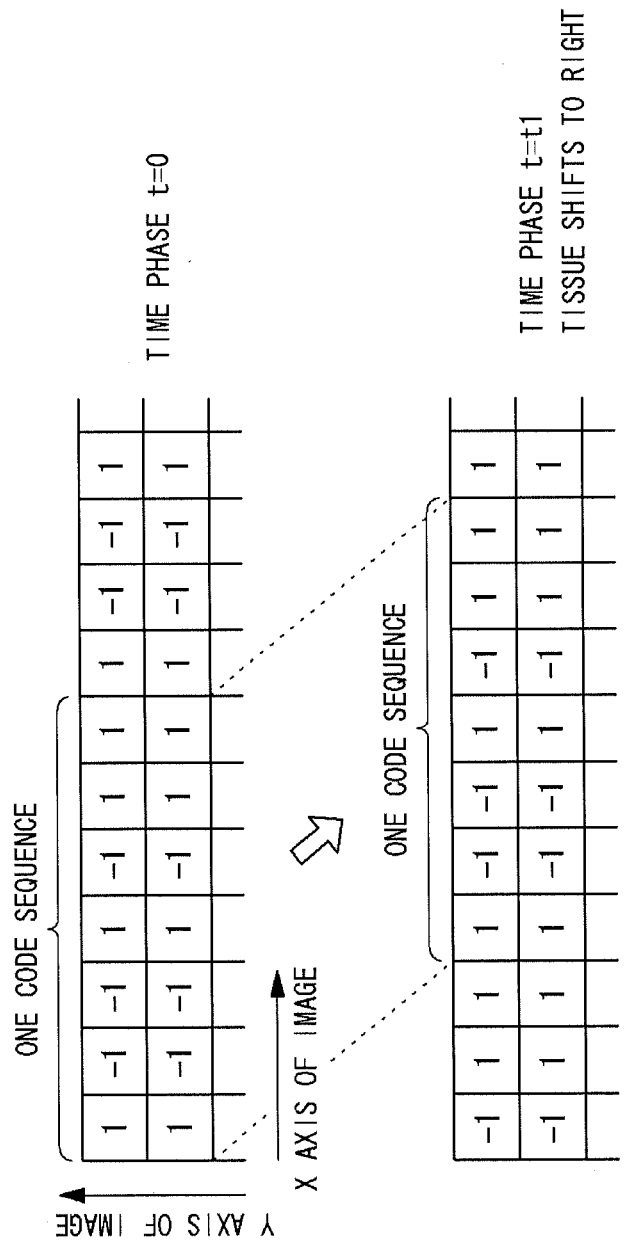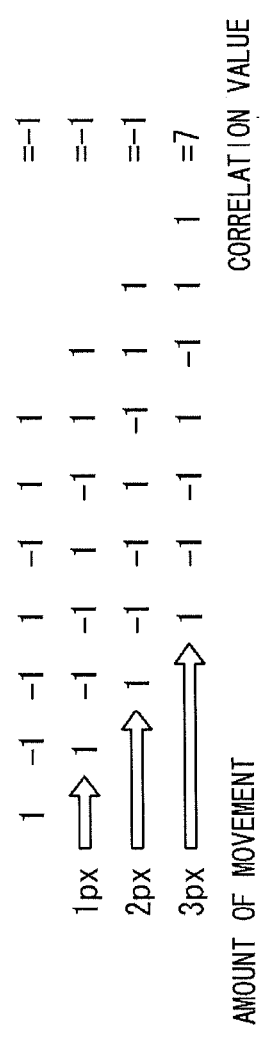
FIG. 20(a)
FIG. 20(b)
FIG. 20(c)

1st TIME PHASE (SHIFT BY 0.25 PIXEL TO LEFT)

ACTUAL POSITION OF
IMAGING TARGET $f_W=0.75$  $f_W=0$  $f_W=0.25$
$f_B=0.25$  $f_B=1$  $f_B=0.75$

PIXEL VALUES
IN IMAGING TARGET

2nd TIME PHASE (SHIFT BY 0.5 PIXEL TO LEFT)

ACTUAL POSITION OF
IMAGING TARGET $f_W=0.5 \quad f_W=0 \quad f_W=0.5$
$f_B=0.5 \quad f_B=1 \quad f_B=0.5$

PIXEL VALUES
IN IMAGING TARGET

RELATIONSHIP BETWEEN BLACK AND WHITE REGIONS INCLUDED IN ONE PIXEL, AND AMOUNT OF MOVEMENT (WHITE → BLACK)

RELATIONSHIP BETWEEN BLACK AND WHITE REGIONS INCLUDED IN ONE PIXEL, AND AMOUNT OF MOVEMENT (BLACK→WHITE)

|   | | | 1 | 2 | 3 | 4 | 5 | | | | |
|---|---|---|---|---|---|---|---|---|---|---|---|
|   | | | | | | | | | | | |
|   | | | | | | | | | | | |
| 1 | | | A | B | C | D | E | | | | |
| 2 | | | F | G | H | I | J | | | | |
| 3 | | | K | L | M | N | O | | | | |
| 4 | | | P | Q | R | S | T | | | | |
|   | | | | | | | | | | | |
|   | | | | | | | | | | | |
|   | | | | | | | | | | | |
|   | | | | | | | | | | | |
|   | | | | | | | | | | | |

# METHOD OF ANALYZING MOTION OF IMAGING TARGET BY MEANS OF TAGGED MR IMAGES, AND MRI DEVICE

TECHNICAL FIELD

The present invention relates to a method for analyzing motion of an imaging target by means of tagged MR images, and an MRI device.

BACKGROUND ART

For diagnosis and treatment of cardiac diseases, it is very important to analyze cardiac wall motion. A tagging MRI method (refer to Non-Patent Literature 1) in which tissues of human body are magnetically labeled is often used for specific analysis of cardiac wall motion. In the tagging MRI method, it is possible to analyze three-dimensional cardiac wall motion by analyzing time-series tagged MR images (time-sequentially taken MR images (cine MRI)).

CITATION LIST

[Non Patent Literature]

[NPL 1] Elias A. Zerhouni, David M. Parish, Walter J. Rogers, Andrew Yang, Edward P. Shapiro, Human Heart: Tagging with MR Imaging—A Method for Noninvasive Assessment of Myocardial Motion. Radiology 169, 59-63, October, 1988

[NPL 2] Albert Montillo, Dimitris Metaxas, Leon Axel, Extracting Tissue deformation using Gabor filter banks, SPIE Vol. 5369, Bellingham, Wash., 2004

SUMMARY OF THE INVENTION

Problems to be Solved by the Invention

In order to analyze motion of an imaging target in the tagging MRI method, it is necessary to perform, as post-processing after taking tagged MR images, extraction of a cardiac wall region as the imaging target, and detection of tag positions by image processing. Lattice-shaped magnetic labels are called "tags", and the contrast of the tags is lowered with time. Therefore, the tag position detection process requires a method resistant to low SN (Signal to Noise ratio) images.

Non-Patent Literature 2 proposes a method utilizing Gabor filter banks, and the like. This method utilizes spatial spread of tags, and therefore, is effective for analyzing global motion of tissue. However, this method is likely to cause analysis error when used for analysis of local motion of tags.

The present invention has an object to provide a technique which enables analysis of motion of an imaging target by means of tagged MR images, based on an idea different from extracting tags by image processing.

Solution to the Problems

The present invention provides a method for analyzing motion of an imaging target by means of tagged MR images, and the method includes the steps of: performing, on the same motion of an imaging target, $N_L$ ($N_L$: positive integer not less than 2) times of cine imaging by means of different tag patterns, to obtain $N_L$ pieces of time-series tagged MR images taken for a plurality of time phases in the motion of the imaging target; arranging $N_L$ pieces of pixel values of the same pixel in the $N_L$ pieces of tagged MR images at each time phase into a pixel value sequence having a length $N_L$ for the corresponding pixel; and analyzing the motion of the imaging target in the time-series tagged MR images by detecting pixels whose pixel value sequences constitute the same code sequence in different time phases. Each of the tag patterns is formed such that the pixel value sequence constitutes a predetermined code sequence. According to the present invention, the motion of the imaging target can be analyzed by tracking the code sequence.

The time phase means a phase of a motion of an imaging target, and a motion to be imaged includes a plurality of phases. For example, an imaging target is caused to repeat a motion such as displacement or deformation by a plurality of times, and the same motion is taken by a plurality of times of cine imaging. In this case, among a plurality of cine images taken by the plurality of times of cine imaging, images in the same time phase (motion phase) represent the same state (position, shape, or the like) of the imaging target. On the other hand, among the plurality of cine images, images in different time phases (motion phases) may represent different states (positions, shapes, or the like) due to the motion of the imaging target.

It should be noted that the pixels include three-dimensional voxels as well as two-dimensional pixels. Further, the pixel value may be a luminance value signal or a phase value signal.

In the step of analyzing motion of the imaging target, preferably, a ratio of each of a plurality of code sequences which coexist in each pixel is calculated based on the pixel value sequence, and an amount of motion of the imaging target in a region less than the size of one pixel is calculated based on the ratio. In this case, the motion can be analyzed in a region less than the size of one pixel.

Another aspect of the present invention provides a method for analyzing motion of an imaging target by means of tagged MR images, and the method includes the steps of: performing, on an imaging target, cine imaging by means of a predetermined tag pattern, to obtain time-series tagged MR images taken in a plurality of time phases of a motion of the imaging target; arranging pixel values of $N_L$ ($N_L$: positive integer not less than 2) pieces of pixels included in the tagged MR image in each time phase into a pixel value sequence having a length $N_L$ for a region comprising the $N_L$ pieces of pixels; and analyzing the motion of the imaging target in the time-series tagged MR images by detecting regions whose pixel value sequences constitute the same code sequence in different time phases. The predetermined tag pattern is formed such that the pixel value sequence constitutes a predetermined code sequence. Also in this case, the motion of the imaging target can be analyzed by tracking the code sequence.

The code sequence preferably has a high noise resistance. For example, the code sequence is preferably an orthogonal code sequence. Alternatively, the code sequence is preferably a spread code sequence, more preferably a PN sequence, and even more preferably an M sequence.

Still another aspect of the present invention provides an MRI device capable of executing the above-described steps.

Effects of the Invention

According to the present invention, motion of an imaging target can be analyzed by tracking a code sequence.

BRIEF DESCRIPTION OF THE DRAWINGS

FIG. 5 is a diagram illustrating a manner of performing a plurality of times of cine imaging.
FIG. 9 is a diagram illustrating tag patterns.
FIG. 10 is a diagram illustrating an example of assignment of code sequences to pixels.
FIG. 14 is a diagram illustrating shifting of a black/white boundary in a first time phase.
FIG. 15 is a diagram illustrating shifting of a black/white boundary in a second time phase.
FIG. 20 is a diagram illustrating a modification of the present invention (coding in an image direction (one-dimensional coding)).

DESCRIPTION OF EMBODIMENTS

Hereinafter, a preferred embodiment of the present invention will be described with reference to the attached drawings.

[1. Structure of MRI Device]

An MRI device 1 according to the present embodiment is able to perform image taking based on a position information coding MRI method of the present invention. Since the position information coding MRI method according to the present embodiment utilizes the tagging MRI method in which an imaging target (e.g., tissue of human body) is magnetically labeled (tagged), the MRI device 1 is configured so as to perform image taking based on the tagging MRI method. It should be noted that, as tags to be superimposed on the imaging target, stripe-shaped or lattice-shaped tags in an arbitrary direction can be generated.

Further, in the present embodiment, cardiac wall motion is adopted as an example of motion of an analysis target. However, motion of the imaging target or analysis target of the present invention is not limited thereto.

Figure 1:
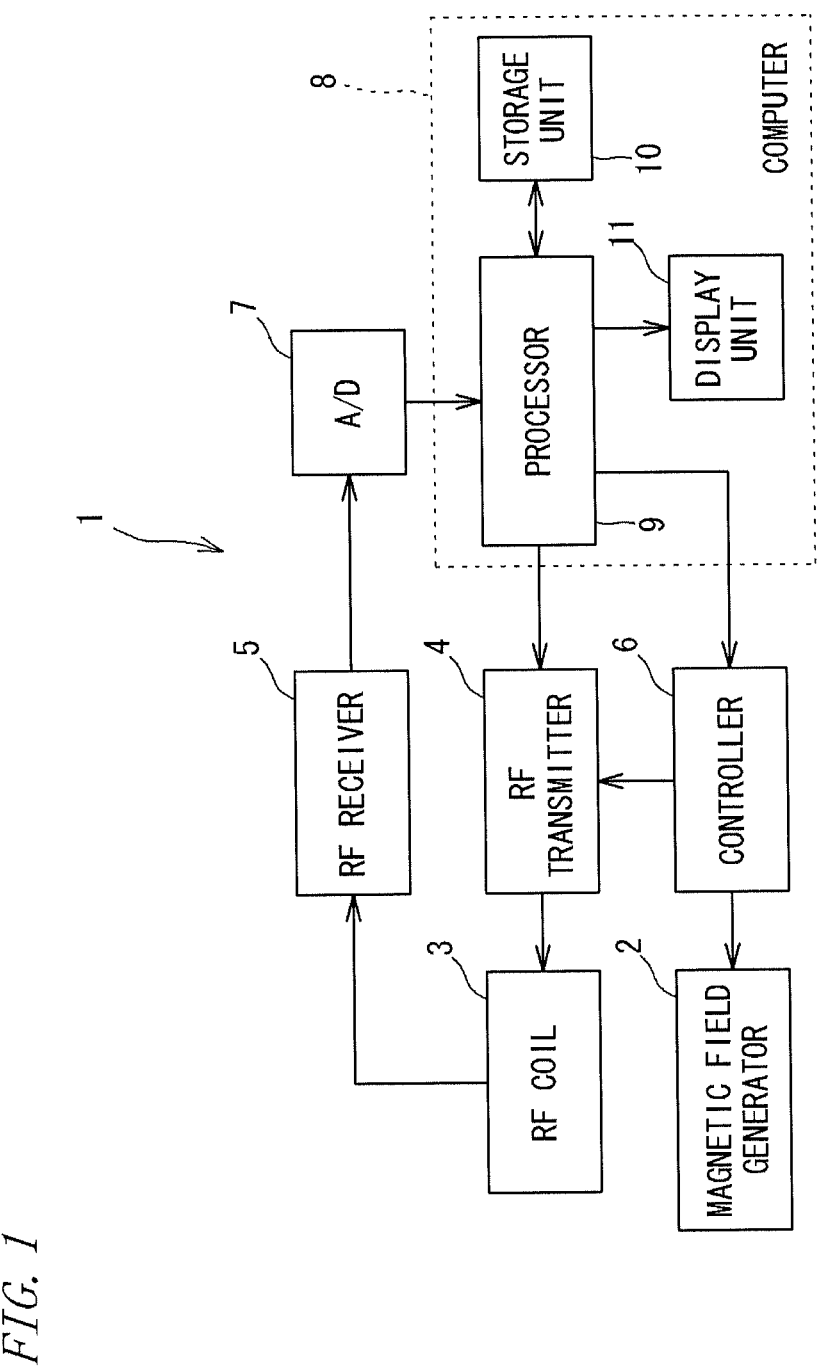
FIG. 1 is a block diagram illustrating the entirety of an MRI device.

As shown in FIG. 1, the MRI device 1 includes a magnetic field generator 2 for generating a static magnetic field or a gradient magnetic field, and an RF coil 3 for transmitting an RF pulse to the imaging target, and receiving a signal generated in the imaging target.

The MRI device 1 further includes an RF transmitter 4 for generating a predetermined RF pulse to be transmitted from the RF coil 3, and an RF receiver 5 for processing a signal (MRI signal) received by the RF coil 3. A tag pulse sequence is generated by a combination of the RF pulse generated by the RF transmitter 4 and transmitted from the RF coil 3, and a gradient magnetic field generated by the magnetic field generator 2.

Generation of the magnetic field by the magnetic field generator 2 and transmission of the RF pulse by the RF transmitter 4 are controlled by a controller 6.

The MRI signal outputted from the RF receiver 5 is supplied to a computer 8 via an A/D converter 7. Based on the obtained MRI signal, the computer 8 performs image processing, motion analysis described later, and the like.

Further, the computer 8 gives necessary instructions to the RF transmitter 4 and the controller 6 to control them.

The computer 8 includes a processor 9, a storage unit 10 having an internal storage device and/or an external storage device, and a display unit 11 including a display and the like. A computer program for controlling the MRI device 1, a computer program for motion analysis of an imaging target, and other necessary computer programs are installed in the storage unit 10. The processor executes these programs to realize the below-described processes.

[2. Motion Analysis]

Figure 2:
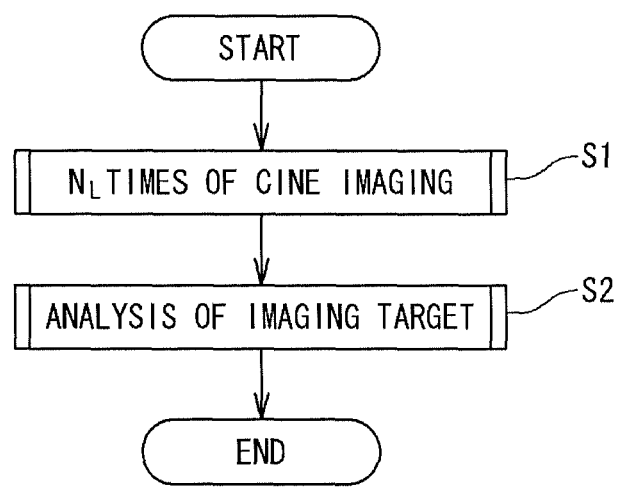
FIG. 2 is a flowchart illustrating process steps performed by the MRI device.

FIG. 2 illustrates a procedure of motion analysis of an imaging target (heart) by the MRI device 1. The motion analysis is divided roughly into: an imaging process (step S1) in which the MRI device 1 performs a plurality of times ($N_L$ times) of cine imaging (imaging of moving picture); and an analysis process (step S2) in which the computer 8 analyzes motion of the imaging target, based on $N_L$ pieces of cine MR images (time-series MR images) obtained in the imaging process.

[2.1. Imaging Process]

In the imaging process at step S1, $N_L$ times of cine imaging are repeatedly performed for the same motion of the same imaging target within the same imaging range. The $N_L$ times of imaging are performed using $N_L$ types of tag patterns. That is, in the imaging process at step S1, $N_L$ pieces of time-series tagged MR images (cine tagged MR images) are obtained, which represent the same motion of the imaging target but have different tag patterns.

Figure 3:
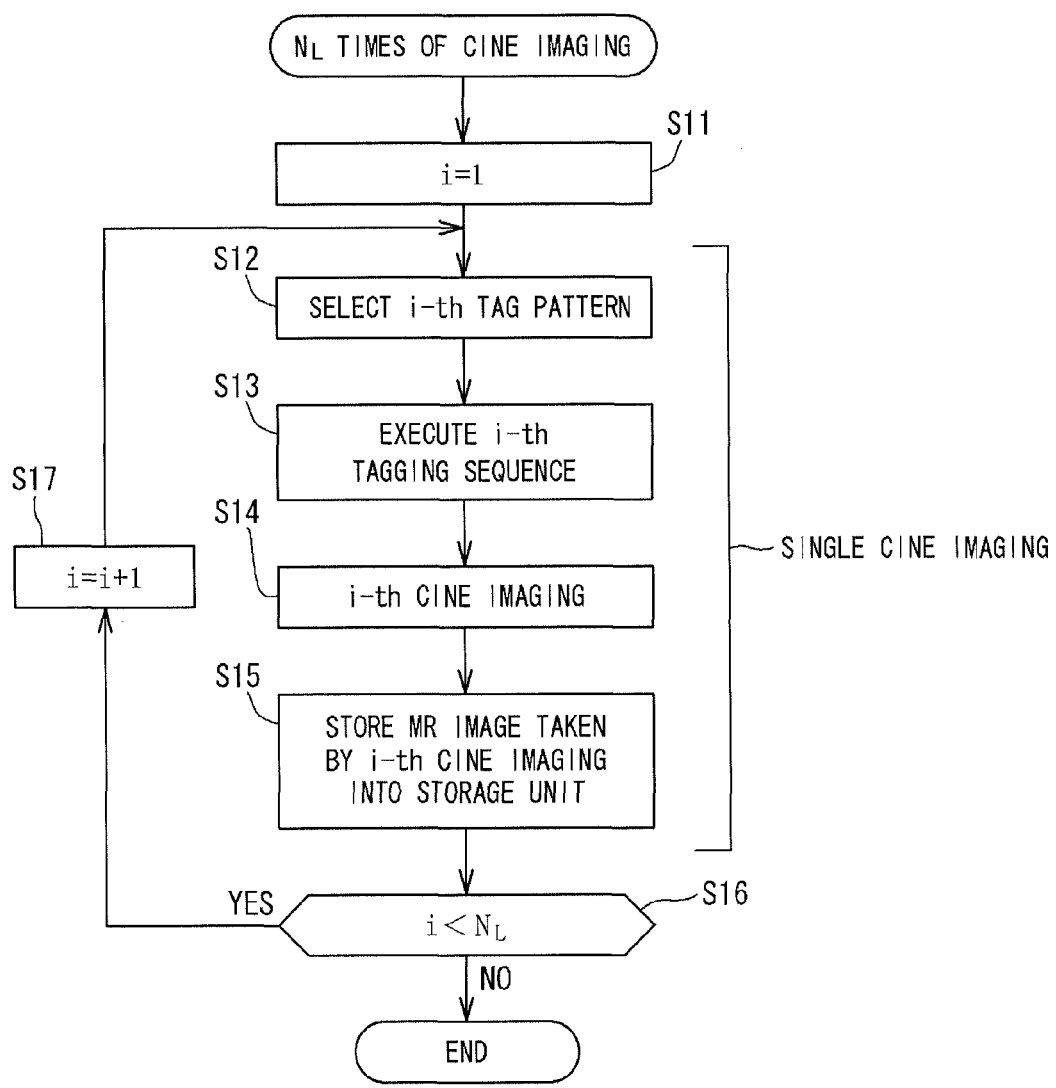
FIG. 3 is a flowchart illustrating cine imaging.

Specifically, as shown in FIG. 3, the imaging process at step S1 includes a loop process (steps S11, S16, and S17) for repeating a single cine imaging (steps S12 to S15) until i (=1) becomes $N_L$ (by $N_L$ times). A process (steps S12 to S15) for each cine imaging is provided in this loop.

In the cine imaging process (steps S12 to S15), firstly, the computer 8 selects a tag pattern to be used for imaging (step S12). $N_L$ types of tag patterns, from the first tag pattern to the $N_L$-th tag pattern, are stored in the storage unit 10 of the computer 8, and the i-th tag pattern is selected for the i-th (i: 1 to $N_L$) cine imaging. The $N_L$ types of tag patterns will be described later in detail.

Then, the computer 8 causes the transmitter 4 to generate an RF pulse which constitutes an i-th tagging sequence for the selected i-th tag pattern, and causes the RF coil 3 to transmit the RF pulse, and further, causes the magnetic field generator 2 to generate a predetermined gradient magnetic field which constitutes the i-th tagging sequence (step S13). Subsequently, the computer 8 executes a process for performing the i-th cine imaging (step S14). A time-series tagged MR image obtained by the cine imaging is stored in the storage unit 10 of the computer 8 (step S15).

Figure 4:
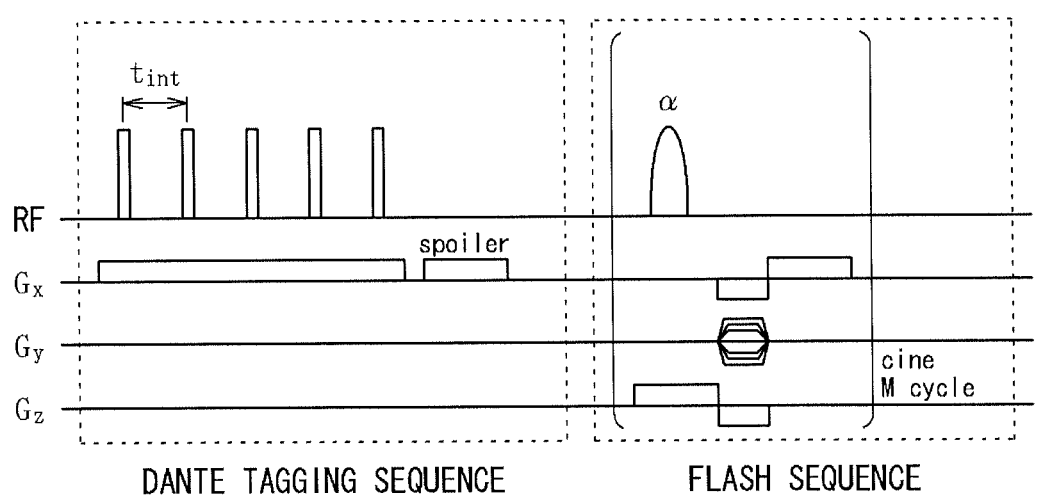
FIG. 4 is a pulse sequence diagram for MRI imaging.

FIG. 4 illustrates a pulse sequence obtained when the cine imaging process (steps S12 to S15) is performed one time. This pulse sequence is a sequence based on a FLASH method (FLASH sequence), and a DANTE tagging sequence for generating the selected tag pattern is added to a preparation part of the FLASH sequence.

The FLASH sequence shown in FIG. 4 is for single taking of a still tagged MR image. The FLASH sequence shown in FIG. 4 is repeated by M times per cine imaging, thereby obtaining a time-series tagged MR image comprising M pieces of still tagged MR images. Assuming that a single still tagged MR image corresponds to a single time phase, a time-series tagged MR image comprising M pieces of still tagged MR images is a time-series tagged MR image for M time phases.

It should be noted that, for example, the FLASH sequence may have an echo time TE=12 ms, and may use, as an excitation RF pulse, a hermite pulse having a flip angle $\alpha=30°$.

Further, a square-wave pulse is used as an excitation RF pulse in the DANTE tagging sequence. In order to obtain a desired tag pattern, an interval $t_{int}$ of square-wave pulses in the DANTE tagging sequence is appropriately set, and an offset frequency $f_0$ or a phase offset for each RF pulse is appropriately set. The pulse interval $t_{int}$ and $G_x$ are in reverse proportion to the interval $d_{int}$ of tags (low-luminance tagged portions in the image). The offset frequency $f_n$ or the phase offset of each RF pulse causes a center frequency position of each tag to shift to an arbitrary position. By designing, utilizing the above characteristics, tagging sequences each having appropriately set pulse interval $t_{int}$ and offset frequency $f_0$, desired $N_L$ types of tag patterns can be obtained.

It should be noted that the MRI imaging sequence is not limited to the FLASH sequence, and the sequence for generating tag patterns is not limited to the DANTE sequence.

FIG. 5(a) illustrates a pulse sequence obtained when the single cine imaging process (steps S12 to S15) shown in FIG. 4 is performed by $N_L$ times. The first tagging sequence to the $N_L$-th tagging sequence shown in FIG. 5(a) each correspond to the DANTE tagging sequence shown in FIG. 4. However, the first to $N_L$-th tagging sequences are used for generating different tag patterns.

In addition, the first cine (#1) to the $N_L$-th cine (#$N_L$) shown in FIG. 5(a) each correspond to the FLASH sequence shown in FIG. 4, and are used for performing the first cine imaging (#1) to the $N_L$-th cine imaging (#$N_L$), respectively.

In each of the respective (first to $N_L$-th) times of cine imaging (the first cine (#1) to the $N_L$-th cine (#$N_L$)), an image of the same motion of the imaging target is taken.

That is, when the imaging target is a heart which beats as shown in FIG. 5(b), a single cine imaging is performed during a period corresponding to one heartbeat, for example. Each cine imaging is performed at the same timing (time phase) with respect to the heartbeat cycle.

As a result, the same motion of the heart is taken in each cine imaging. Accordingly, in the time-series tagged MR images taken by the respective (first to $N_L$-th) times of cine imaging, the position and shape of the heart are the same in the same time phase.

[2.2 Analysis Process]

In the analysis process at step S2, the computer 8 performs analysis of the motion of the imaging target, based on the $N_L$ pieces of time-series tagged MR images obtained in the imaging process at step S1.

Figure 6:
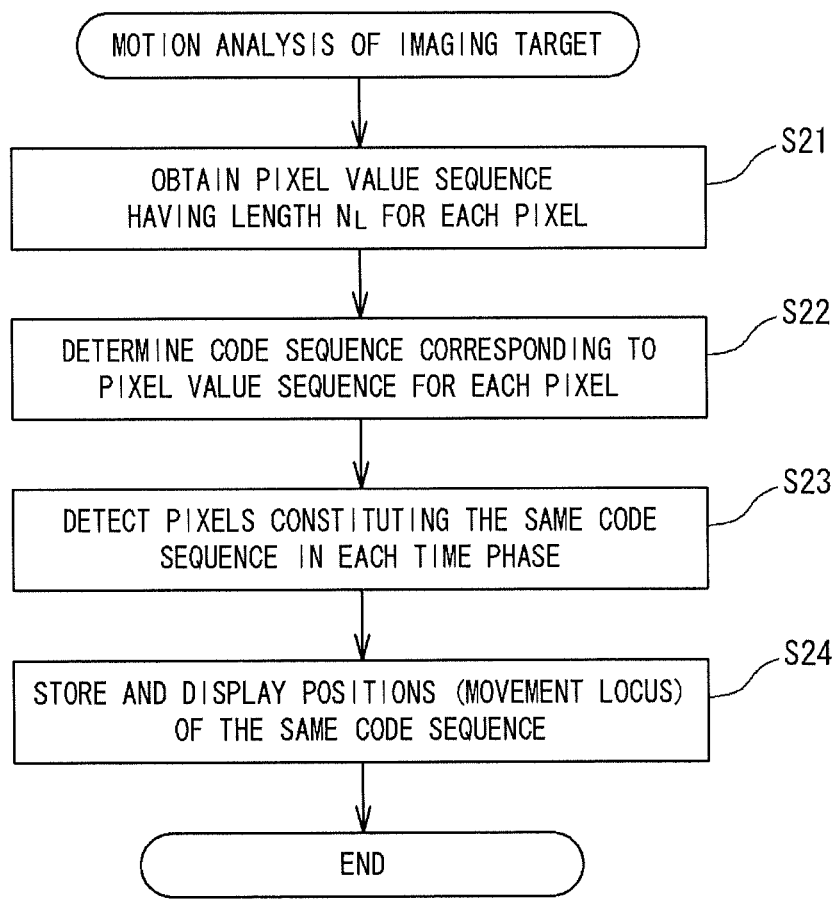
FIG. 6 is a flowchart illustrating analysis of motion of an imaging target.

Specifically, as shown in FIG. 6, firstly, the computer 8 performs a process of arranging the $N_L$ pieces of pixel values existing for each of the pixels of the tagged images into a pixel value sequence having a length $N_L$ (a signal of a length $N_L$) for the corresponding pixel (step S21). Although each pixel value is a luminance value of a pixel, it may be a phase value of the pixel.

Figure 7:
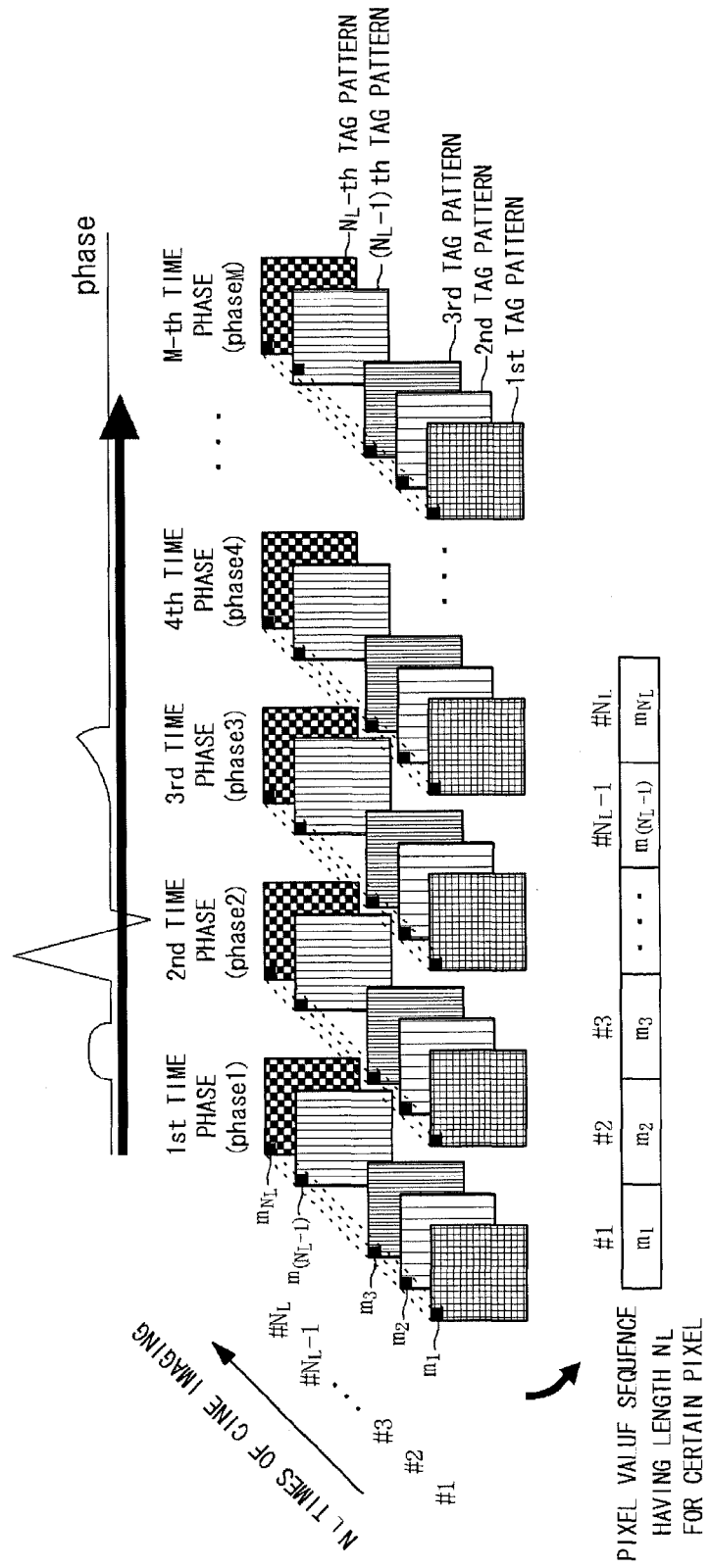
FIG. 7 is a diagram illustrating a manner of generating pixel value sequences from a plurality of times of cine imaging.

As shown in FIG. 7, when the $N_L$ pieces of time-series tagged MR images are arranged according to the time phases, $N_L$ pieces of tagged images are obtained for each time phase. Accordingly, when focusing attention on individual pixels of the tagged images, $N_L$ pieces of pixel values exist for each pixel in each time phase. These $N_L$ pieces of pixel values are arranged in the order of imaging to obtain a pixel value sequence having a length $N_L$.

When a low-luminance region (black region) where a tag exists is regarded as "+1" while the other region (white region) is regarded as "−1", the pixel value sequence having a length $N_L$ (a signal having a length $N_L$) can be regarded as a sequence obtained by modulating the pixel values into a code sequence having a length $N_L$. That is, a code sequence is assigned to each pixel in the first time phase. Accordingly, when the imaging target does not move, if a code sequence assigned to a pixel can be identified, the position of the pixel can be identified. Further, a tag is superimposed on the imaging target itself, and moves in association with motion of the imaging target. Therefore, movement of the tag can be tracked when the computer 8 determines a code sequence corresponding to the pixel value sequence of each pixel by calculation of correlation functions described later (step S22), and detects and tracks the positions of pixels constituting the same code sequence in the respective time phases (step S23). Accordingly, analysis of motion of the imaging target is realized without performing the conventional image processing for detecting the tag position.

Specifically, the positions of pixels having the same code sequence in the respective time phases are stored in the storage unit 10, and the movement locus of the pixels having the same coding sequence are displayed on the display unit 11. Thus, a user of the device 1 can accurately get the manner of motion of the imaging target.

Figure 8:
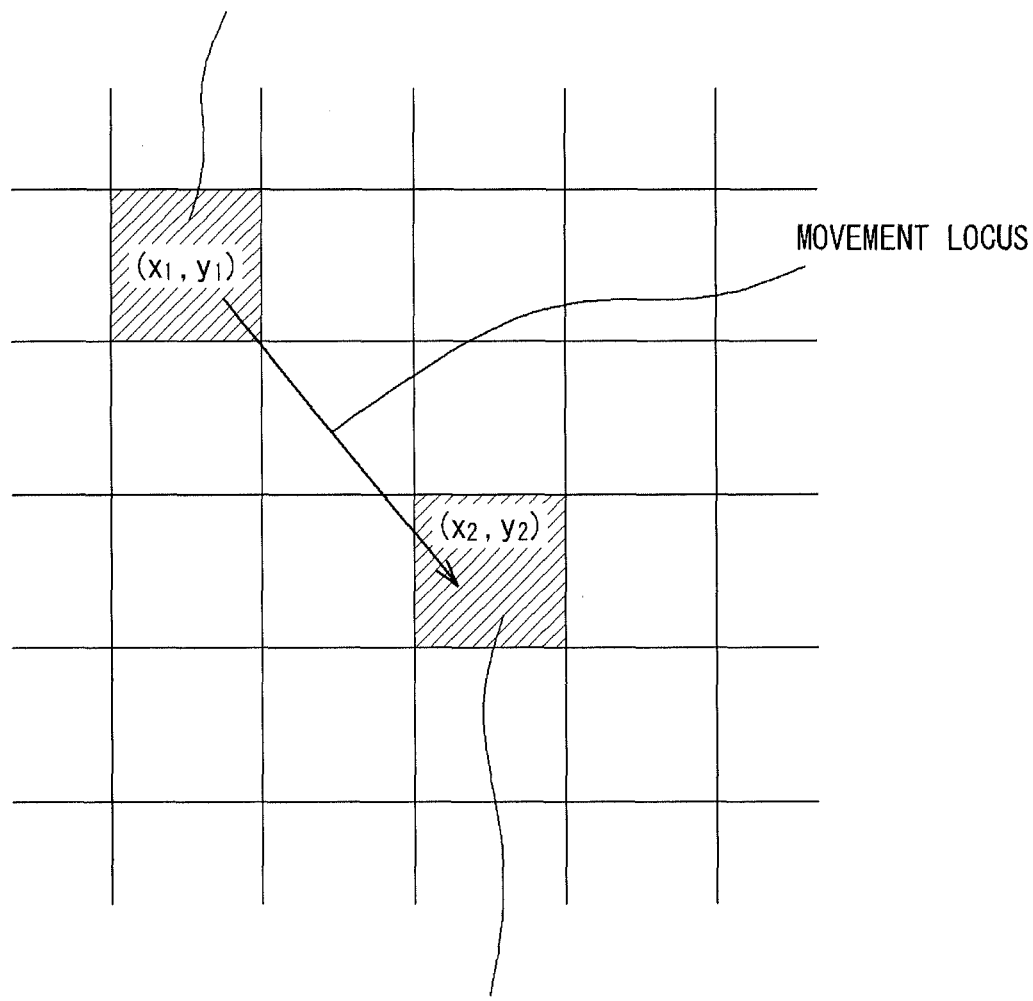
FIG. 8 is a diagram illustrating tracking of pixel motion.

For example, as shown in FIG. 8, a case where movement of a part of the imaging target, which part is indicated by a pixel $(x_1, y_1)$ in the first time phase, is considered. When a code sequence corresponding to the pixel value sequence of the pixel $(x_1, y_1)$ in the first time phase is a code sequence $L_1$, pixels having the pixel value sequence corresponding to the code sequence $L_1$ in the respective time phases are specified, thereby obtaining a movement locus indicating how the part of the imaging target, indicated by the pixel $(x_1, y_1)$ in the first time phase, has moved over the time phases from the first time phase to the $N_L$-th time phase.

In FIG. 8, it is assumed that the position information (code sequence $L_1$) assigned to the pixel $(x_1, y_1)$ in the tag pattern in the initial time phase (first time phase) is present at a pixel $(x_2, y_2)$ in the $M_X$-th time phase due to motion of the imaging target.

In this case, the pixel $(x_1, y_1)$ in the initial time phase can be regarded as a transmitter station which has transmitted the code sequence $L_1$, and the pixel $(x_2, y_2)$ in the $M_X$-th time phase can be regarded as a receiver station which has received the code sequence $L_1$ transmitted from the transmitter station. In communication, the receiver station can identify the code sequence indicated by the received signal (pixel value sequence) by decoding the received signal.

Accordingly, in the present embodiment, the above-described tracking of the movement locus is identical to detection of the receiver station (pixel) which has received the code sequence $L_1$.

Further, in the tagged MR images, the tag contrast is lowered with passage of time. Therefore, the pixel value sequence of the pixel in the $M_X$-th time phase has a low SN, which is similar to poor communication environment. However, in communication, selecting an appropriate coding sequence can deal with such poor communication environment. Likewise, selecting an appropriate code sequence can deal with such lowering of the tag contrast in the tagged MR images.

In the conventional method of extracting a tag region by image processing, a low-luminance region corresponding to the tag region is detected. Therefore, to be exact, only the boundary of the tag region is subjected to motion analysis, while the other region should be subjected to motion estimation by interpolation. In order to perform accurate motion estimation by the conventional method, both the tag region and the non-tag region should be reduced in size. However, considering the relationship between the pixel size and the widths of the tag region and the non tag region, or considering that the boundary between these regions is not an exact rectangle, if the widths of the tag region and the non-tag region are reduced, the contrast between these regions is lowered, resulting in a difficulty in detecting the tag region. Therefore, in the tagging MRI for performing cardiac wall motion analysis, it is general to use a pattern in which a tag region and a non-tag region, whose total width is about 6 mm, are repeated.

However, since the thickness of cardiac wall is about 10 mm, only two tag regions appear at a maximum, which makes it difficult to accurately examine a difference in motion in the direction parallel to the thickness of cardiac wall.

However, in the method according to the present embodiment, since the position information of all the pixels is coded, motion analysis within the pixel size is realized for all the pixels. Consequently, accurate motion analysis is realized.

[3. Available Code Sequences]

By using a code sequence having a high noise resistance and a high interference resistance as the above-described code sequence, the position of a pixel to which the code sequence is assigned can be identified with high accuracy. For example, it is possible to perform spread spectrum (SS) by means of spread codes as the code sequence. The spread spectrum is a communication technique including: modulating a narrowband modulation signal into a wideband signal having several hundred to several thousand times of spectrum by means of spread codes; transmitting the wideband signal; converting the wideband signal into the original narrowband signal at a receiver end; and demodulating the narrowband signal. The SS has an interference resistance, and a resistance to poor transmission channels.

By utilizing the property of the SS that it resistant to poor transmission channels, highly-accurate motion analysis is realized against reduction in tag contrast with passage of time.

There are two conditions necessary for a code sequence to be used for the SS. One condition is that an autocorrelation is steep at a phase difference $\tau=0$, and a correlation is sufficiently small at phase differences other than $\tau=0$. This condition is necessary for uniformly spreading the spectrum. The other condition is that a correlation between code sequences is sufficiently small at all phase differences. This condition is necessary for suppressing co-channel interference. One of sequences satisfying these conditions is a pseudo noise (PN) sequence. The narrow definition of the PN sequence is that it is a periodic sequence whose autocorrelation takes only two-level values, and that it is a periodic sequence in which the number of "+1" and the number of "−1" in one period differ only by one. An M sequence is known as a typical PN sequence. In the present embodiment, the M sequence is adopted as a code sequence.

It should be noted that each of the above-described spread code sequence, PN sequence, and M sequence has an orthogonality in which codes are almost orthogonal to one another, and therefore, is also regarded as an orthogonal code sequence.

[4. Calculation of Correlation Function for Identifying Code Sequence from Pixel Value Sequence]

[4.1. Calculation of Correlation Function]

An aggregate of code sequences (number of code sequences=$N_s$) each having a length $N_L$ is denoted by L. An i-th code sequence in the code sequence aggregate L is denoted by $L_i$ ($1 \leq i \leq N_s$), and each code element is denoted by $l_{ij}$ ($1 \leq i \leq N_s$, $1 \leq j \leq N_L$), where $l_{ij} \in \{1, -1\}$ is satisfied. A result obtained by spreading an information code $S\hat{} \in \{1, -1\}$ with the spread code sequence $L_i$ is $S^{(i)} = \{S_j^{(i)}\}$ ($1 \leq j \leq N_L$). At this time, $S_j^{(i)} = S\hat{} \times l_{ij} \in \{1,-1\}$ is satisfied.

A correlation function $\Phi_k$ between a code sequence $L_k$ and $S_j^{(i)}$ is calculated as follows. However, since only a phase difference $\tau=0$ occurs in the method of the present embodiment, the correlation function is calculated at only $\tau=0$. Further, $S\hat{}$ is 1 for simplification.

[Math. 1]

$$\Phi_k = \sum_j l_{kj} \times S_j^{(i)} \qquad (1)$$

In formula (1), $\Phi_k$ is $N_L$ when i is k, and $\Phi_k$ is −1 when i is not k. Accordingly, k with which the result of calculation of $\Phi_k$ (k=1, 2, . . . , $N_s$) takes a maximum value is a number of the assigned code sequence. However, in actual communication environment, $S_j^{(i)}$ cannot be transmitted as it is, and therefore, is often modulated into an analog signal. Here, a correlation function is considered taking into account the influence of analog modulation. Assuming that "A" denotes a depth of modulation and "B" denotes a signal intensity at non-modulation, a modulated reception signal $s_j^{(i)}$ is B when $S_j^{(i)}$ is −1, and B−A when $S_j^{(i)}$ is 1, and therefore, $s_j^{(i)}$ is represented as follows.

[Math. 2]

$$s_j^{(i)} = -A \times \frac{1+S_j^{(i)}}{2} + B \qquad (2)$$

At this time, a correlation function $\phi_k$ between the modulated signal and the code sequence $L_k$ is represented as follows.

[Math. 3]

$$\phi_k = \sum_j l_{kj} \times s_j^{(i)}$$

$$= -\frac{A}{2} \sum_j l_{kj} \times S_j^{(i)} + \sum_j l_{kj} \times \left(B - \frac{A}{2}\right)$$

If the code sequence $L_k$ is an M sequence,
[Math. 4]

$$\Sigma_{j=1}^{N_L} l_{kj} = -1$$

is satisfied, and therefore, $\phi_k$ is represented by
[Math. 5]

$$\phi_k = -A' \times \Phi_k - (B-A') \qquad (3)$$

where, $A/2=A'$. Accordingly, if A and B take constant values, k with which the result of calculation of $\Phi_k$ (k=1, 2, ..., $N_s$) takes a minimum value is a number of the assigned code sequence. That is, it is possible to identify a code sequence by means of a modulated signal.

[4.2. Calculation of Correlation Function in Embodiment]

It is assumed that, for a certain FOV (Field Of View), cine imaging is performed for M time phases, with a resolution $W_{MTX}$ [pixel] and an inter-time-phase interval $t_{ph}$ [sec]. A pixel value (image signal) of a pixel (x, y) at time $t=t_{ph} \times p$ is represented by a(x, y, p). Since the time of the initial time phase (first time phase) is $t=t_{ph} \times 0$, p satisfies $0 \leq p \leq M-1$.

Now, a spread code sequence $L_i = \{l_{ij}\}$ having a length $N_L$ is considered. When the pixel value a(x, y, p) and the spread code $l_{ij}$ (j=1, 2, ..., $N_L$) are multiplied, a pixel value $g^{(i)}$(x, y, p, j) modulated by spread spectrum is obtained. The obtained pixel value $g^{(i)}$(x, y, p, j) of the image is replaced by $m_j^{(i)}$ for simplification, and modulation by means of the MRI tagging method is considered, $m_j^{(i)}$ is represented as follows.

[Math. 6]

$$m_j^{(i)} = -\frac{1+l_{ij}}{2} \times k_1 + k_2 \qquad (4)$$

In formula (4), $k_1$ corresponds to a pixel value contrast between a tag region and a non-tag region, and $k_2$ corresponds to the pixel value of the non-tag region. Ideally, these values are constants. When $l_{ij}$ is 1, $m_j^{(i)}$ is $k_2-k_1$, which indicates a low luminance in the image. On the other hand, when $l_{ij}$ is −1, $m_j^{(i)}$ is $k_2$, which indicates a high luminance in the image. Accordingly, by appropriately setting the tag region, the pixel value in the MRI imaging can be modulated by spread spectrum.

At this time, a correlation function $\phi_k$ between the pixel value $m_j^{(i)}$ ($1 \leq j \leq N_L$) and the code sequence $L_k$ is represented by

[Math. 7]

$$\phi_k = \sum_j l_{kj} \times m_j^{(i)}$$

and, if $k_1/2$ is $k'_1$, $\phi_k$ is represented as follows.
[Math. 8]

$$\phi_k = -k'_1 \times \Phi_k - (k_2 - k'_1) \qquad (5)$$

Accordingly, k with which $\phi_k$ takes a minimum value indicates a code sequence used for modulation of the corresponding pixel. By tracking the pixels having the minimum $\phi_k$ over the time phases from the first time phase to the $N_L$-th time phase, movement of the pixel positioned at (x, y) in the initial time phase can be tracked.

In actual imaging by means of the MRI device 1, however, $k_1$ and $k_2$ vary among the images corresponding to the respective elements of the code sequences, depending on the condition of the imaging. Moreover, $k_1$ and $k_2$ also vary depending on the pixel position. Therefore, formula (4) of [Math. 6] is actually represented as follows.

[Math. 9]

$$m_j^{(i)}(x, y) = -\frac{1+l_{ij}}{2} \times k_1(x, y, j) + k_2(x, y, j) \qquad (6)$$

In this case, formula (5) of [Math. 8] is not satisfied, which makes it difficult to identify the assigned code sequence $L_i$. So, in order to eliminate the influences due to the pixel position and the imaging condition, division of the pixel value $m_j^{(i)}$ is performed as follows.

[Math. 10]

$$\tilde{m}_j^{(i)}(x, y) = -\frac{1+l_{ij}}{2} \times \frac{k_1(x, y, j)}{k_2(x, y, j)} + 1 \qquad (7)$$

Assuming that $k_1$(x,y,j)/$k_2$(x,y,j) is $k_3$(x,y,j), $k_3$ corresponds to the tag contrast. If $k_3$(x,y,j) is almost constant regardless of j, the correlation function $\phi_k$ is represented by

[Math. 11]

$$\phi_k = -\frac{\Phi_k - 1}{2} \times k_3(x, y, j) - 1 \qquad (8)$$

and, also in this case, a code sequence corresponding to each pixel can be identified by obtaining k with which $\phi_k$ takes a minimum value.

[5. Examples of Tag Patterns]

In the present embodiment, M sequences are used as code sequences. Each M sequence has a code length of $N_L=2^n-1$, and the number of M sequences is $N_L=2^n-1$. In each M sequence, the ratio between the autocorrelation value and the cross-correlation value at $\tau=0$ is $-N_L:1$. In the present embodiment, when identifying a code sequence from a pixel value sequence, it is desirable that the autocorrelation value has a peak, and therefore, $N_L$ is desired to be large. On the other hand, when $N_L$ is large, it takes a long time to take $N_L$ pieces of time-series tagged MR images. So, in the present embodiment, $N_L$ is 7.

As M sequences satisfying $N_L=7$, code sequences generated by a binary primitive polynomial, $x^2+x+1$, are used. In the above-described DANTE tagging sequence (or SPAMM tagging sequence), a periodic tag pattern in which a tag region having a constant length and a non-tag region having a constant length are alternately repeated is realized. Therefore, by selecting code sequences from among the generated seven M sequences and spatially arranging the code sequences in an appropriate manner, a periodic tag pattern is realized for the entire imaging process.

The present embodiment adopts a code arrangement in which six code sequences selected from among the seven code sequences are arranged. That is, Ns is 6. The following Table 1 shows the six M sequences $L_1$ to $L_6$.

TABLE 1

| | 1st code sequence $L_1$ | 2nd code sequence $L_2$ | 3rd code sequence $L_3$ | 4th code sequence $L_4$ | 5th code sequence $L_5$ | 6th code sequence $L_6$ |
|---|---|---|---|---|---|---|
| 1st tagging sequence | −1 | 1 | −1 | 1 | −1 | 1 |
| 2nd tagging sequence | 1 | −1 | −1 | 1 | −1 | −1 |
| 3rd tagging sequence | 1 | 1 | 1 | −1 | −1 | −1 |
| 4th tagging sequence | −1 | −1 | 1 | 1 | 1 | −1 |
| 5th tagging sequence | 1 | −1 | −1 | −1 | 1 | 1 |
| 6th tagging sequence | −1 | −1 | 1 | −1 | −1 | 1 |
| 7th tagging sequence | −1 | 1 | −1 | −1 | 1 | −1 |

In Table 1, each horizontal line corresponds to a single tag pattern. FIG. 9 shows seven tag patterns (each pattern is an enlarged view of a part (comprising 18×18 pixels) of the image) obtained when DANTE tagging sequences are designed such that, in Table 1., "−1" represents a high-luminance region while "1" represents a low-luminance region corresponding to a tag.

In each of the tag patterns shown in FIG. 9, code sequences $L_1$ to $L_6$ are assigned to the respective pixels in the corresponding image region (comprising 18×18 pixels) as shown in FIG. 10. Each of the code sequences $L_1$ to $L_6$ assigned to each pixel indicates the position information of the pixel.

Using the code sequences shown in Table 1 allows coding of position information without error up to a period of time about twice as long as the longitudinal relaxation time T1 of the imaging target, for example.

In FIG. 10, the same code sequence is assigned to the pixels in each vertical line. This is because all the plurality of tag patterns are designed to be vertical-stripe patterns, for simplification. However, in FIG. 10, different code sequences may be assigned to the pixels in each vertical line. In order to cause the adjacent pixels in the horizontal direction and the vertical direction have different code sequences, horizontal-stripe patterns and lattice patterns are included in the plurality of tag patterns. Such tag patterns can also be generated by appropriately setting the tagging sequences.

[6. Result of Experiment]

Figure 11C:
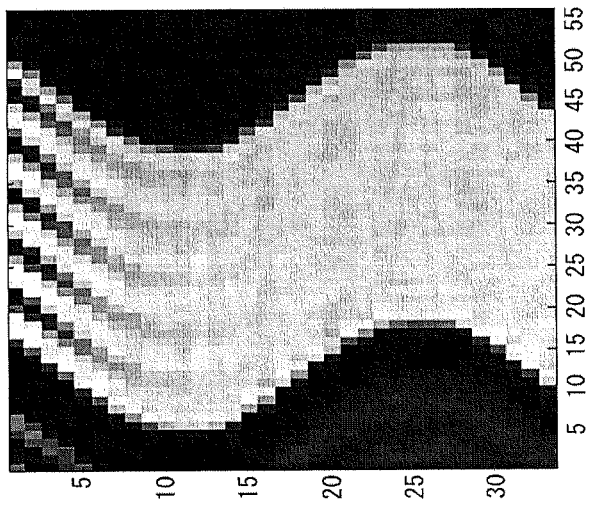
FIG. 11 illustrates photographs of images showing experimental results.
Figure 11B:
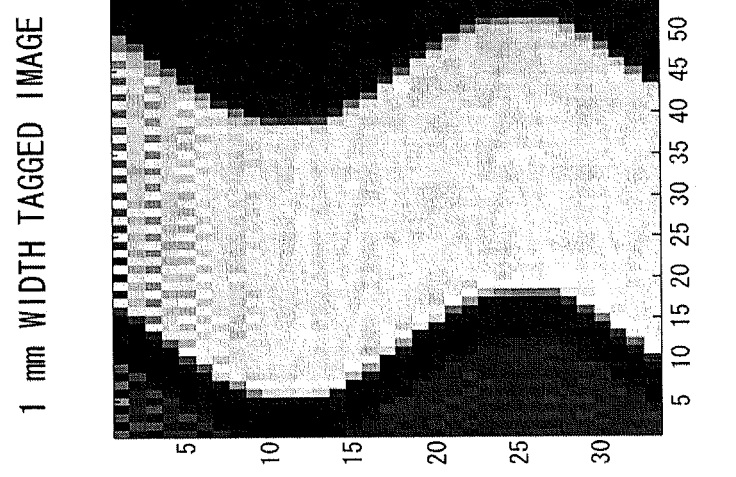
Figure 11A:
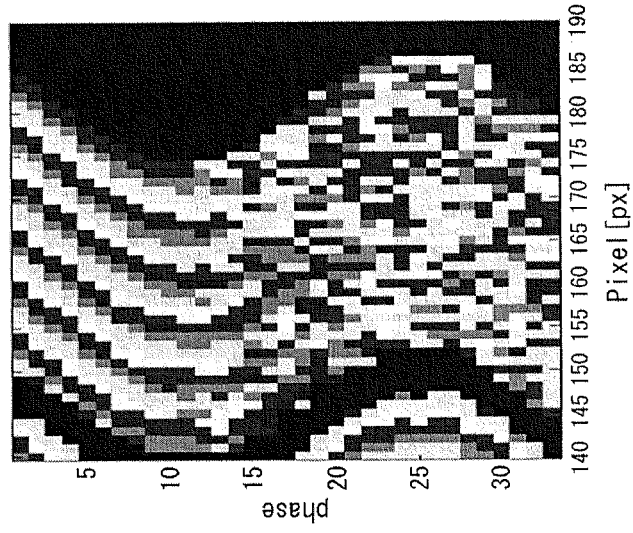
Figure 12:
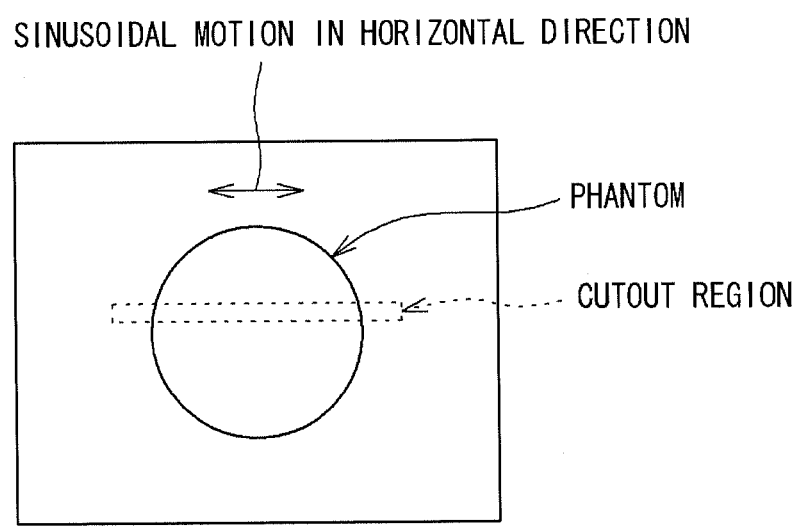
FIG. 12 is a diagram illustrating how an imaging target (phantom) moves.

FIGS. 11(a) to 11(c) show the images of a phantom (imaging target) shown in FIG. 12 which sinusoically moves in the horizontal direction, taken by the tagging MRI device 1.

Seven cine images are taken by the MRI device 1 using the seven tag patterns shown in FIG. 9 ($N_L=7$), and displacement of the position of the phantom is determined in the above-described M sequences satisfying $N_L=7$. The result of the determination is shown in FIG. 11(a).

In FIG. 11(b), in the time-series images (from the first time phase to the thirty-third time phase) of the phantom which sinusoidally moves in the horizontal direction, regions at the same position (each region comprising 1 pixel in the vertical direction×about 50 pixels in the horizontal direction) are cut out from the images in the respective time phases, and thus obtained strip-shaped regions are arranged in the longitudinal axis direction of FIG. 11 along the time (time phase). That is, the vertical axis of FIG. 11(a) indicates the time (from the first time phase to the thirty-third time phase), and the horizontal axis thereof indicates the pixel position.

In FIG. 11(a), the determined code sequences $L_1$ to $L_6$ are distinguished based on the brightness of the pixels. That is, in FIG. 11(a), pixels of the same brightness are pixels determined as having the same code sequence.

FIG. 11(b) shows, among the seven cine images constituting the M sequences, an image obtained by taking the phantom using a tag pattern in which the horizontal width of each tag region (low-luminance region) and the horizontal width of each non-tag region (high-luminance region) are 1 mm (corresponding to one pixel). Assuming that the width of one pixel is 1 mm, the tag pattern shown in FIG. 11(b) corresponds to the first tag pattern shown in FIG. 9.

FIG. 11(c) shows, among the seven cine images constituting the M sequences, an image obtained by taking the phantom using a tag pattern in which the horizontal width of each tag region (low-luminance region) and the horizontal width of each non-tag region (high-luminance region) are 3 mm (corresponding to three pixels). Assuming that the width of one pixel is 1 mm, the tag pattern shown in FIG. 11(c) corresponds to any of the third to fifth tag patterns shown in FIG. 9.

Also in FIGS. 11(b) and 11(c), regions at the same position (each region comprising 1 pixel in the vertical direction× about 50 pixels in the horizontal direction) are cut out from the images in the respective time phases, and thus obtained strip-shaped regions are arranged in the longitudinal axis direction of FIG. 11 along the time (time phase).

As shown in FIG. 11(a), in the determination result of the tagged MR image by means of the M sequences, movement of the phantom (sinusoidal motion in the horizontal direction) can be determined almost exactly, at 1 mm (1 pixel) intervals, up to near the thirteenth or fourteenth time phase (up to thirteenth or fourteenth line from the top).

On the other hand, in the 1 mm wide tagged MRI image shown in FIG. 11(b), since both the tag region and the non-tag region are narrow, the contrast between these regions are lowered, and the tag pattern disappears by the tenth time phase, which disables further tracking.

In the 3 mm wide tagged MRI image shown in FIG. 11(c), like the determination result obtained by the M sequences, the tag pattern can be tracked with faint contrast up to the thirteenth or fourteenth time phase. However, since the tag pattern is wide, the resolution of the position determination is not more than 3 mm.

As described above, in the case where the tag pattern itself of the original image is tracked as shown in FIGS. 11(b) and 11(c), the available time for position detection might be reduced, or the detection accuracy might be degraded. On the other hand, in the code determination by means of the $N_L$ pieces of images shown in FIG. 11(a), the position of the imaging target can be detected for a relatively long period with a relatively high accuracy.

[7. Sub-Pixel Analysis]

In the above-described determination by means of the M sequences, analysis is performed pixel by pixel (pixel analysis), and the accuracy of position detection is on a pixel basis. Accordingly, an amount of movement less than one pixel cannot be detected.

Figure 13:
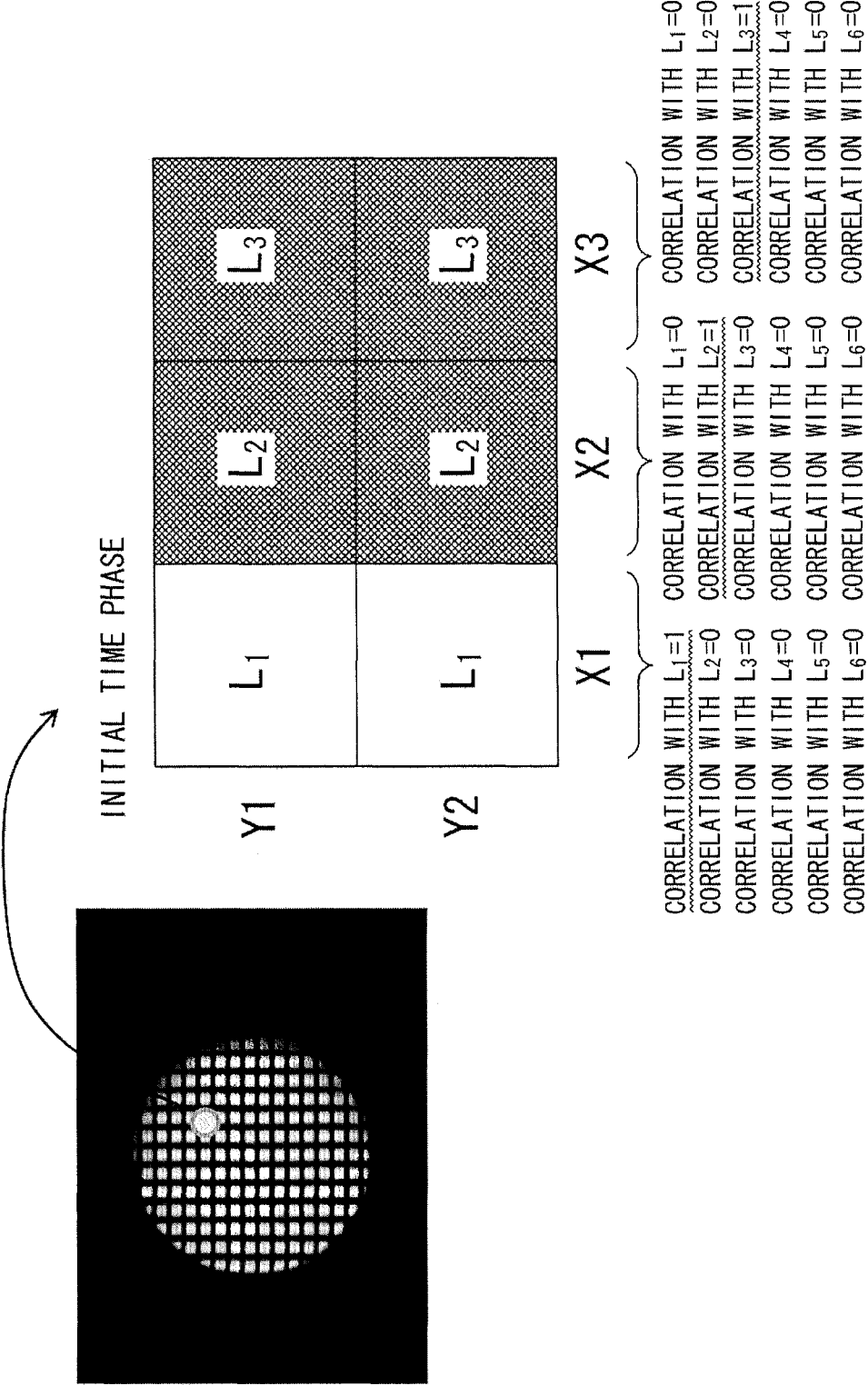
FIG. 13 is a diagram illustrating a pixel boundary and a black/white boundary in an initial time phase.

FIG. 13 is an enlarged view of a part of a time-series tagged MR image in the initial time phase (first time phase), obtained by taking an image of a target (phantom) to which a tag pattern is applied. FIG. 13 shows 6 pixels, i.e., horizontal three pixels (X1, X2, X3)×vertical two pixels (Y1, Y2).

As shown in FIG. 13, in the initial time phase, the boundary between a low-luminance region (black region) and a high-luminance region (white region) in the tag pattern applied to the imaging target coincides with the boundary of pixels. In FIG. 13, the horizontal width of the black region just corresponds to two pixels.

However, if the imaging target moves with passage of time, the low-luminance region (black region) and the high-luminance region (while region) are mixed in each pixel in the taken image of the imaging target. FIG. 14 shows the actual position of the imaging target which has moved by 0.25 pixel to the left from the position shown in FIG. 13, and the pixel values in the taken image. FIG. 15 shows the actual position of the imaging target which has moved by 0.5 pixel to the left from the position shown in FIG. 13, and the pixel values in the taken image.

In FIG. 14, the imaging target has moved by 0.25 pixel to the left as shown in FIG. 14(a). However, the pixel value (luminance value) is obtained only on a pixel basis. Therefore, regarding the pixel values in the taken image, as shown in FIG. 14(b), the pixel X2 becomes a black region, but the pixel X1 becomes a region of light gray in which black is slightly mixed into white, and the pixel X3 becomes a region of dark gray in which white is slightly mixed into black. In FIGS. 13 to 15, a mesh drawn in each pixel corresponds to the magnitude of the pixel value (luminance). The rougher the mesh is, the closer to white (high luminance) the pixel is. The finer the mesh is, the closer to black (low luminance) the pixel is.

Further, in FIG. 15, the imaging target has moved by 0.5 pixel to the left as shown in FIG. 15(a). Regarding the pixel values in this case, as shown in FIG. 15(b), the pixel X2 becomes a black region, but the pixels X1 and X3 become regions of gray intermediate between white and black.

Although the horizontal width of the black region originally corresponds to two pixels as shown in FIG. 13, when the imaging target has moved by less than one pixel, the boundary between the black region and the white region blurs as shown in FIGS. 14(b) and 15(b).

Even when the boundary between the both regions is unclear, the above-described code-sequence detection (code determination) is performed pixel by pixel. Accordingly, assuming that, in the initial time phase shown in FIG. 13, the pixel X1, the pixel X2, and the pixel X3 correspond to the first code sequence $L_1$, the second code sequence $L_2$, and the third code sequence $L_3$, respectively, there is a high possibility that, in the state shown in FIG. 14, the pixel value sequences of the pixel X1, the pixel X2, and the pixel X3 might be detected as the first code sequence $L_1$, the second code sequence $L_2$, and the third code sequence $L_3$, respectively, as in FIG. 13. In this case, even though the imaging target has moved by 0.25 pixel to the left, it is determined that the imaging target has not moved at all.

Further, in the state shown in FIG. 15, there is a high possibility that the detection result might be similar to that of FIG. 14, or the pixel value sequences of the pixel X1, the pixel X2, and the pixel X3 might be detected as the second code sequence $L_2$, the third code sequence $L_3$, and the fourth code sequence $L_4$, respectively. In the former case, even though the imaging target has moved by 0.5 pixel to the left, it is determined that the imaging target has not moved at all. In the latter case, even though the imaging target has moved by 0.5 pixel to the left, it is determined that the imaging target has moved by one pixel.

Sub-pixel analysis to obtain an amount of movement less than one pixel is performed such that, in step S22 shown in FIG. 6, instead of determining a single code sequence from the pixel value sequence of each pixel, code sequence detection is performed considering a possibility that a plurality of code sequences ($L_1$ to $L_6$) might coexist in each pixel.

In order to perform code sequence detection considering a possibility that a plurality of code sequences ($L_1$ to $L_6$) might coexist in each pixel, correlation values between the pixel value sequence of each pixel and the respective code sequences ($L_1$ to $L_6$) are used.

A correlation value between the pixel value sequence and a specific code sequence is represented by a value between "0" to "1", and "1" indicates the highest correlation while "0" indicates the lowest correlation.

When the boundary of pixels coincides with the boundary between the black and white regions of the imaging target as in the initial time phase shown in FIG. 13, a plurality of code sequences do not coexist in each pixel, and the pixel value sequence corresponds to a single code sequence. Accordingly, the correlation values between the pixel value sequence of each pixel and the respective code sequences ($L_1$ to $L_6$) are theoretically as shown in FIG. 13. Specifically, the pixel X1 has the highest correlation with the first code sequence $L_1$, and has the lowest correlation with the other code sequences $L_2$ to $L_6$. The pixel X2 has the highest correlation with the second code sequence $L_2$, and has the lowest correlation with the other code sequences $L_1$ and $L_3$ to $L_6$. The pixel X3 has the highest correlation with the third code sequence $L_3$, and has the lowest correlation with the other code sequences $L_1$, $L_2$ and $L_4$ to $L_6$.

When the imaging target has moved by 0.25 pixel to the left as shown in FIG. 14(a), a plurality of code sequences coexist in each pixel. Accordingly, the correlation value between the pixel value sequence of each pixel and each of the respective code sequences ($L_1$ to $L_6$) is theoretically a value according to the magnitude of the area of a region occupied by the code sequence in the pixel.

As shown in FIG. 14(a), in the pixel X1, the first code sequence $L_1$ and the second code sequence $L_2$ coexist. Therefore, the correlation with the first code sequence $L_1$ is 0.75, and the correlation with the second code sequence $L_2$ is 0.25, while the correlations with the other code sequences $L_3$ to $L_6$ take the minimum value. In this way, the pixel X1 has the correlations with the code sequences $L_1$ and $L_2$ according to the magnitudes of the areas of regions occupied by the code sequences $L_1$ and $L_2$. Likewise, the pixel X2 (X3) has the correlations with a plurality of code sequences which coexist in the pixel, according to the magnitudes of the areas of regions occupied by the code sequences.

Further, when the imaging target has moved by 0.5 pixel to the left as shown in FIG. 15(a), in the pixel X1, the correlation with the first code sequence $L_1$ is 0.5, and the correlation with the second code sequence $L_2$ is 0.5, while the correlations with the other code sequences $L_3$ to $L_6$ take the minimum value. In this way, the pixel X1 has the correlations with the code sequences $L_1$ and $L_2$ according to the magnitudes of the areas of regions occupied by the code sequences $L_1$ and $L_2$. Likewise, the pixel X2 (X3) has the correlations with a plurality of code sequences which coexist in the pixel, according to the magnitudes of the areas of regions occupied by the code sequences.

The processor 9 identifies one or a plurality of code sequences ($L_1$ to $L_6$) included in each pixel, based on the correlation values of the pixel with the respective code sequences ($L_1$ to $L_6$) as shown in FIGS. 14 and 15, and obtains the ratio of each code sequence in the pixel.

Figure 16:
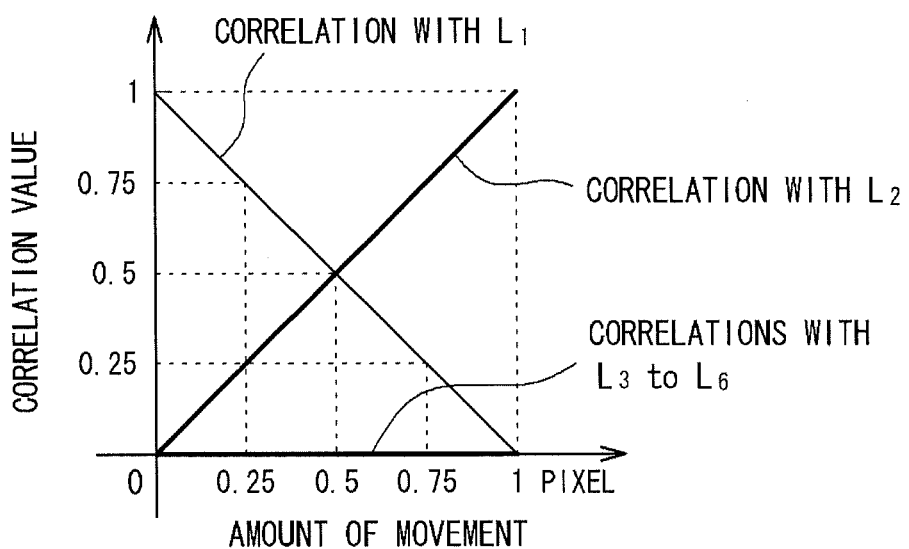
FIG. 16 is a diagram illustrating the relationship between a code sequence correlation value and an amount of movement.
Figure 17:
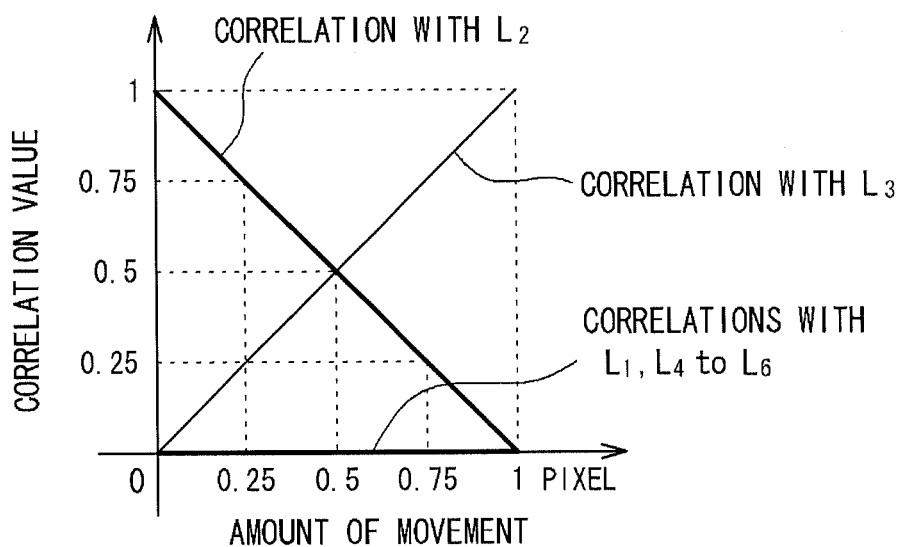
FIG. 17 is a diagram illustrating the relationship between a code sequence correlation value and an amount of movement.
Figure 18:
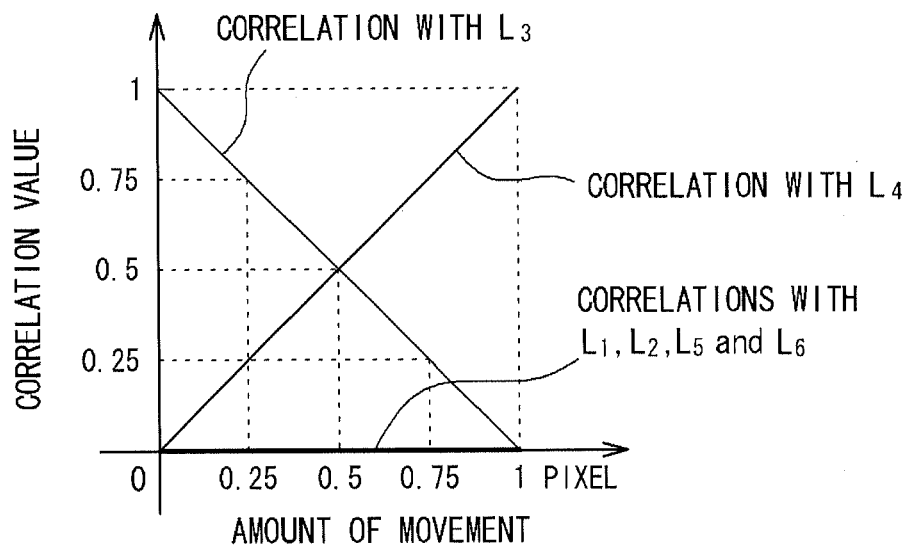
FIG. 18 is a diagram illustrating the relationship between a code sequence correlation value and an amount of movement.

Specifically, as shown in FIGS. 16 to 18, information (amount-of-movement specifying information) which defines the relationships between the correlation values with the respective code sequences ($L_1$ to $L_6$) and the amount of movement is previously stored in the storage unit 10, and the processor 9 performs code sequence identification or the like with reference to the information shown in FIGS. 16 to 18.

FIG. 16 shows variations of the correlation values between the pixel value sequence of a certain pixel and the respective code sequences ($L_1$ to $L_6$), during a period from a state where only the code sequence $L_1$ exists in the pixel (the position of "0" on the horizontal axis of FIG. 16) to a state where the code sequence $L_2$ shifts into the pixel and the pixel is occupied by only the code sequence $L_2$ (the position of "1 pixel" on the horizontal axis of FIG. 16).

FIG. 17 shows variations of the correlation values between the pixel value sequence of a certain pixel and the respective code sequences ($L_1$ to $L_6$), during a period from a state where only the code sequence $L_2$ exists in the pixel (the position of "0" on the horizontal axis of FIG. 17) to a state where the code sequence $L_3$ shifts into the pixel and the pixel is occupied by only the code sequence $L_3$ (the position of "1 pixel" on the horizontal axis of FIG. 17).

FIG. 18 shows variations of the correlation values between the pixel value sequence of a certain pixel and the respective code sequences ($L_1$ to $L_6$), during a period from a state where only the code sequence $L_3$ exists in the pixel (the position of "0" on the horizontal axis of FIG. 18) to a state where the code sequence $L_4$ shifts into the pixel and the pixel is occupied by only the code sequence $L_4$ (the position of "1 pixel" on the horizontal axis of FIG. 18).

Although FIGS. 16 to 18 show only three pieces of information (amount-of-movement specifying information) relating to the motion of the imaging target shown in FIGS. 13 to 15, actually a plurality of pieces of information as many as the number of combinations of code sequences that might simultaneously exist in one pixel are stored in the storage unit 10.

For example, when the correlations values with the respective code sequences ($L_1$ to $L_6$) as shown in FIG. 14(*a*) are obtained for the pixel X1, the processor 9 searches the plurality of pieces of information (amount-of-movement specifying information) stored in the storage unit 10 for information that fits the obtained correlation values. Since the code sequence of the pixel X1 is the code sequence $L_1$ in the previous time phase (initial time phase; refer to FIG. 13), the information shown in FIG. 16, in which the correlation value with the code sequence L1 is maximum at the position of "0" on the horizontal axis, is selected from among the plurality of pieces of information stored in the storage unit 10.

Then, the processor 9 determines that the amount of movement (shift) of the code sequence $L_2$ is "0.25", based on the state where the correlation value with the code sequence $L_1$ is 0.75 and the correlation value with the code sequence $L_2$ is 0.25, with reference to the information shown in FIG. 16

Likewise, for each of the other pixels shown in FIG. 14(*a*) and the pixels shown in 15(*a*), it is possible to obtain coexisting code sequences and the amount of movement of a code sequence that has shifted into the pixel (the ratio of the code sequence in the pixel).

When the motion of the imaging target is the simple reciprocating motion (sinusoidal motion) in the horizontal direction as shown in FIGS. 13 to 15, the direction of motion of the imaging target can be specified by only the ratio of each code sequence. However, when the motion of the imaging target is more complicated, the direction of the motion can be estimated by verifying the manner of change in the ratio of the code sequence in each pixel over continuous time phases.

In the information (amount-of-movement specifying information) shown in FIGS. 16 to 18, the relationship between the correlation value and the amount of movement is linear, but it is actually non-linear in many cases. When the relationship between the correlation value and the amount of movement is non-linear, it is preferred to use, as amount-of-movement specifying information, a relationship previously obtained by calculation from the code sequences or a relationship previously obtained by actual measurement, for each of the combinations of the code sequences.

The above-described sub-pixel analysis allows calculation of an amount of motion of the imaging target in a region less than the size of one pixel.

Figure 19:
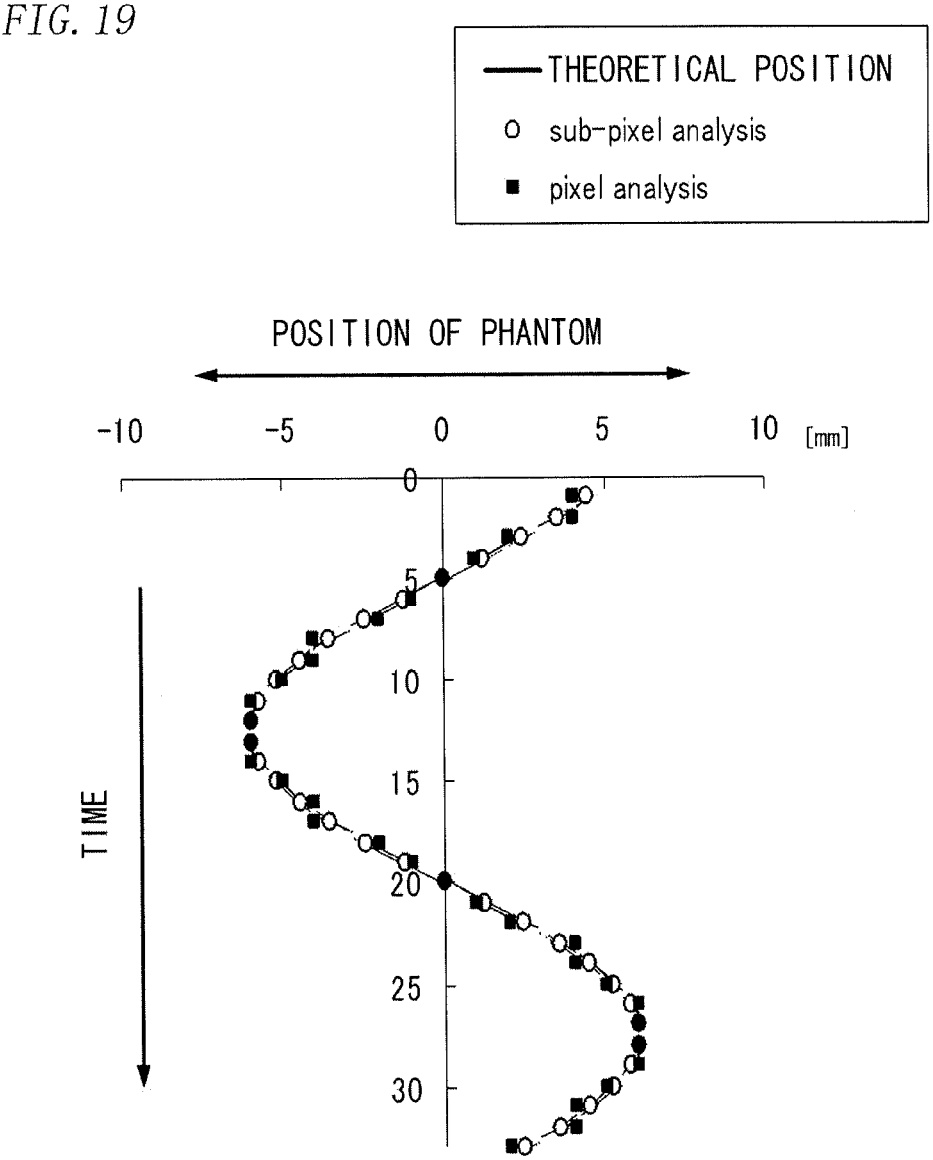
FIG. 19 is a conceptual diagram illustrating a difference between analysis precision of sub-pixel analysis and analysis precision of pixel analysis.

FIG. 19 shows an image of an analysis result which is obtained when sub-pixel analysis and pixel analysis are performed on an imaging target (phantom) which moves sinusoidally in the horizontal direction. When focusing attention on a certain point of the imaging target, the motion of the imaging target is a sinusoidal motion as shown by a solid line (theoretical position) in FIG. 19. When pixel analysis is performed on this imaging target, position detection is performed only in units of 1 mm. On the other hand, in the sub-pixel analysis, a motion less than 1 mm can be detected, and therefore, a position close to the theoretical position can be detected.

[8. Modification]

Although in the above-described embodiment a code sequence (position information) is assigned to each pixel, a target to which a code sequence (position information) is assigned is not limited to a single pixel, but may be an image region comprising a plurality of pixels.

Moreover, when a target to which a code sequence (position information) is assigned is an image region comprising $N_L$ pieces of pixels in a single time-series tagged MR image, the code sequence can be formed, not in the $N_L$ direction, but in an image direction (in X direction or Y direction of a two-dimensional image, or in X direction, or Y direction, or Z direction of a three-dimensional image). In this case, it is not necessary to take a plurality of time-series tagged MR images, and thus the image-taking time is shortened.

FIG. 20 shows an example in which a code sequence "1, −1, −1, 1, −1, 1, 1" is assigned in the image direction (X direction). In this case, a region having the above code sequence, which was positioned at the left end of the image at time phase (time) t=0, has shifted rightward at time phase (time) t=t1 due to a motion of the imaging target (human tissue). At time phase (time) t=t1, in order to detect a region to which the code sequence is assigned, a correlation with the code sequence "1, −1, −1, 1, −1, 1, 1" is obtained in the image at time phase t=t1, and a position where the correlation increases is detected.

For example, as shown in FIG. 20, when considering a case where a correlation is obtained at the same position as the position of the code sequence "1, −1, −1, 1, −1, 1, 1" at time phase t=t1, a case where a correlation is obtained at a position shifted by one pixel to the right from the above position, a case where a correlation is obtained at a position shifted by two pixels to the right and a case where a correlation is obtained at a position shifted by three pixels to the right, the highest correlation is obtained at the position shifted by three pixels to the right, whereas the correlations are −1 (minimum value) in the other cases. Accordingly, it is detected that, at time phase t=t1, the region to which the code sequence "1, −1, −1, 1, −1, 1, 1" is assigned is located at the position shifted by three pixels to the right.

[9. Sub-Pixel Analysis in Modification]

Also in this modification, not only analysis on a pixel basis (pixel analysis) but also analysis for less than one pixel (sub-pixel analysis) is realized. When performing the sub-pixel analysis in this modification, an amount of movement (a ratio of a white region or a black region in each pixel) is obtained from a pixel value (luminance value) of the pixel.

Figure 21:
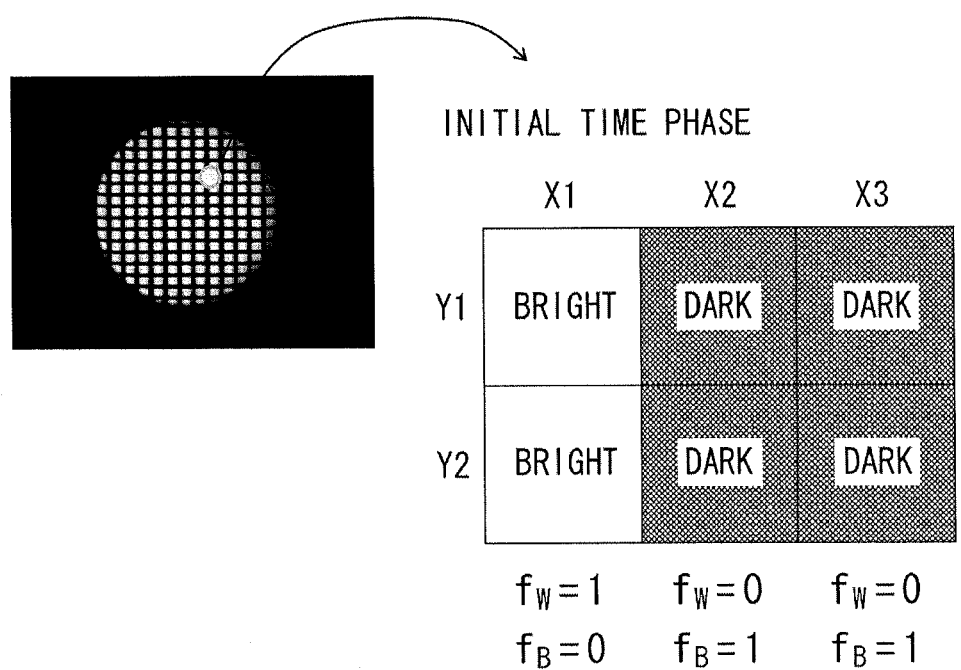
FIG. 21 is a diagram illustrating a pixel boundary and a black/white boundary in the initial time phase.
Figure 22A:
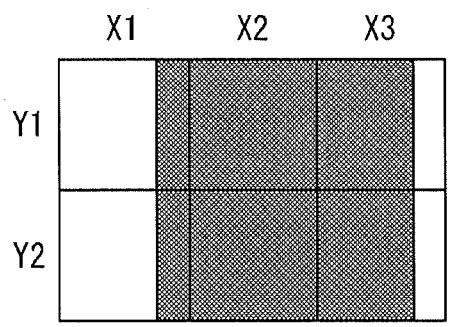
FIG. 22 is a diagram illustrating shifting of a black/white boundary in the first time phase.
Figure 22B:
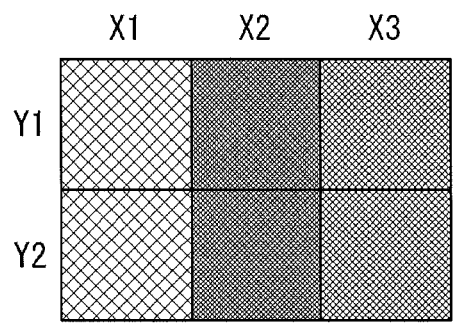
Figure 23A:
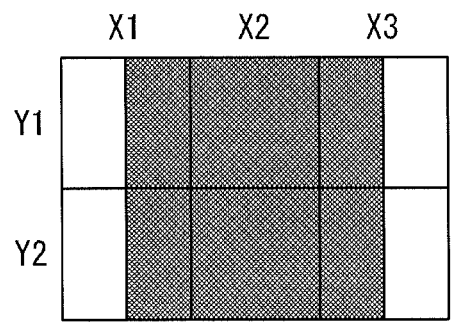
FIG. 23 is a diagram illustrating shifting of a black/white boundary in the second time phase.
Figure 23B:
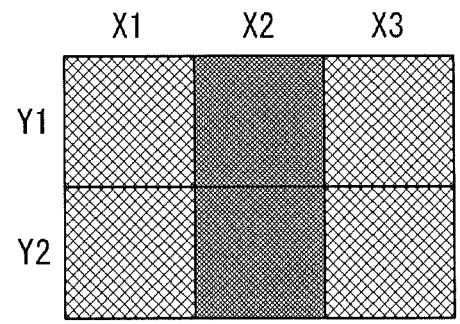

That is, in a tag pattern, when a boundary between a white region and a black region is positioned in one pixel, the pixel has an intermediate color (intermediate luminance) between the white region and the black region as shown in FIGS. 22(b) and 23(b). For example, when a portion of a black region of a next pixel (e.g., a pixel X2 in FIG. 21) shifts into a pixel (e.g., a pixel X1 in FIG. 21) in which only a white region is imaged, the pixel value of the pixel X1 becomes blackish with an intensity according to the size of the black region in the pixel X1.

On the other hand, when a portion of a black region of a next pixel shifts into a pixel (e.g., a pixel X3 in FIG. 21) in which only a black region is imaged, the pixel value of the pixel X3 becomes whitish with an intensity according to the size of the white region in the pixel X3.

Assuming that the luminance of the black region in the tag pattern is "0" while the luminance of the white region is "1", the pixel value (luminance) and the amount of movement in the case where a portion of the black region shifts into a pixel of the white region are shown in FIG. 24(a). On the other hand, the pixel value (luminance) and the amount of movement in the case where a portion of the white region shifts into a pixel of the black region are shown in FIG. 24(b).

Figure 24:
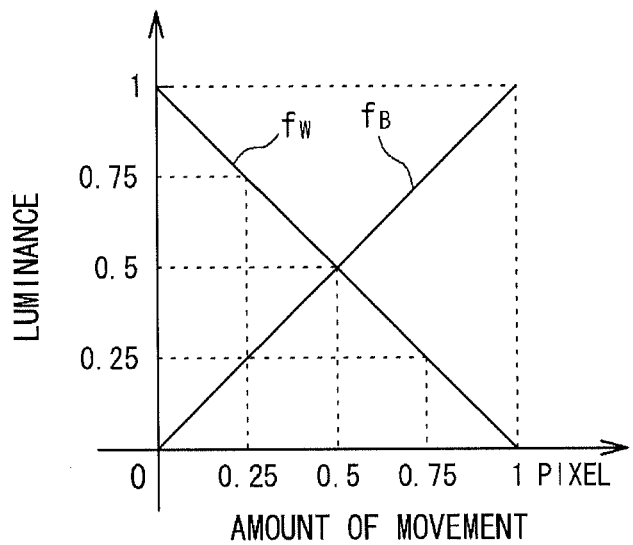
FIG. 24 is a diagram illustrating the relationship between black and white regions and an amount of movement.
Figure 24:
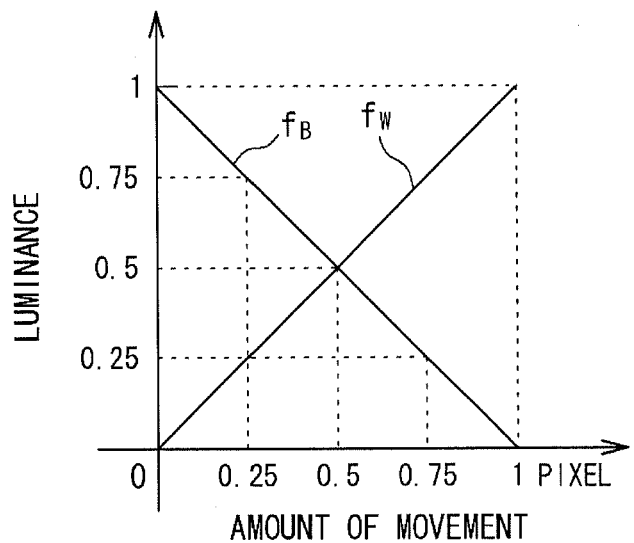

The pixel value shown in FIG. 24 is normalized by a pixel value in a time-series MR image to which no tag pattern is applied for the same motion of the same imaging target. Depending on the position of the imaging target, identical white (black) regions may have different pixel values, or the tag pattern may disappear with passage of time (e.g., the black region becomes the white region). The above-described normalization allows application of the relationship shown in FIG. 24 even when different pixel values (luminance values) are obtained depending on the conditions. Further, the normalization may be performed by means of, not the pixel values in the untagged time-series MR images, but the pixel value of the white or black region in the same time phase or the contrast between them.

In order to obtain an amount of movement by means of the relationship (amount-of-movement specifying information) shown in FIG. 24, firstly, based on the pixel value, a ratio $f_w$ of a white region in a pixel and a ratio $f_B$ of a black region in the pixel are obtained. These ratios $f_w$ and $f_B$ are obtained by normalizing the pixel value of a certain pixel.

For example, in a case where a black region of a tag pattern disappears with passage of time, the value of the black region at each time phase varies so as to approach the value of the white region. A countermeasure against this situation is as follows. In a time-series MR image to which no tag pattern is applied for the same motion of the same imaging target, attention is focused on a pixel (corresponding pixel) in the same time phase and at the same position as a target pixel for which the ratios $f_w$ and $f_B$ are to be calculated. In normalization, the pixel value of the target pixel for which the ratios $f_w$ and $f_B$ are to be calculated is divided by the pixel value of the corresponding pixel. Thereby, the pixel value of the target pixel is normalized by a value between "1" (white region only) to "0" (black region only), and the value becomes $f_W$. The ratio $f_B$ is obtained by calculating $[1-f_W]$.

When the ratios $f_w$ and $f_B$ are obtained, an amount of shift (amount of movement) of the white region or the black region into the target pixel can be obtained by the size less than one pixel, based on the ratios $f_w$ and $f_B$, by means of the relationship shown in FIG. 24. The direction of movement can be estimated based on the location of the white region or the black region in the past time phase, or the pixel values of pixels surrounding the target pixel. However, when assuming a regular sinusoidal motion in the horizontal direction, motion analysis is realized by only the amount of movement.

[Extension of Modification to Two Dimensions (Multiple Dimensions)]

In FIG. 20, a region of pixels to which a code sequence (position information) is assigned is a one-dimensional region (only in the X direction), a code sequence may be assigned to a two-dimensional or three-dimensional region. Further, the direction of the plurality of times (e.g., $N_L$ times) of imaging shown in FIG. 7 may be additionally considered. In this case, as for a two-dimensional image, a code sequence may be assigned to a three-dimensional region including an image X direction, an image Y direction, and an imaging direction. As for a three-dimensional image, a code sequence may be assigned to a four-dimensional region including an image X direction, an image Y direction, an image Z direction, and an imaging direction.

Figures 25A, 25B:
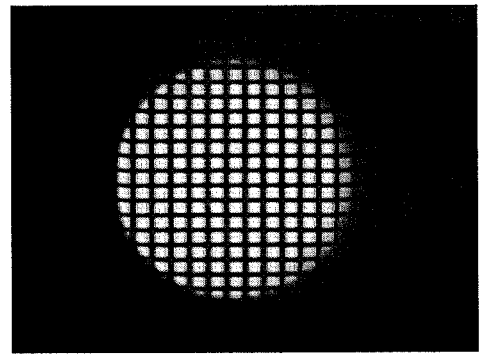
FIG. 25 is a diagram illustrating an example in which the modification is extended two-dimensionally.
Figure 26:
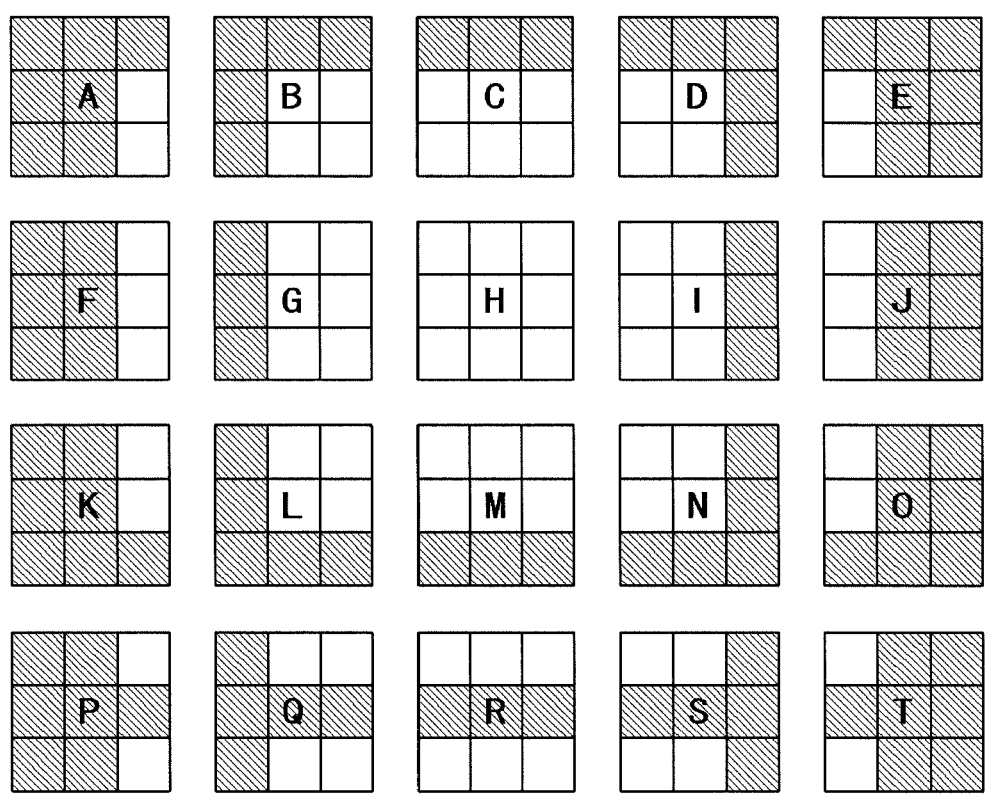
FIG. 26 is a diagram illustrating a list of image patterns each constituting a code sequence in the example of FIG. 25.

FIGS. 25 and 26 show an example in which the modification shown in FIG. 20 is extended to two dimensions. In the example shown in FIGS. 25 and 26, a region of pixels to which one code sequence (position information) is assigned is a two-dimensional region (3 pixels×three pixels).

A tag pattern shown in FIG. 25(a) is a pattern for extending the modification to two dimensions. This pattern has, as shown in FIG. 25(b), horizontal stripes (horizontal stripe pattern) and vertical stripes (vertical stripe pattern). In the pattern shown in FIG. 25(b), when viewed in the vertical direction of the image, the ratio of the white region (white band) width to the black region (black band) width in the horizontal stripe pattern is 3:1. When viewed in the horizontal direction of the image, the ratio of the white region (white band) width to the back region (black band) width in the vertical stripe pattern is 3:2. In FIG. 25(b), hatched portions correspond to the black regions, and blank portions correspond to the white regions.

When such a tag pattern is applied to the imaging target, a black and white pattern, in which a unit of twenty pixels (vertical 4 pixels×horizontal 5 pixels) (A to T in FIG. 25(b)) is repeated in the horizontal and vertical directions, is formed in a two-dimensional space as shown in FIG. 25(a).

With respect to the twenty pixels A to T, black and white patterns are considered, each pattern comprising nine pixels in which each of the pixels A to T is located in the center (i.e., the self pixel and surrounding eight pixels; a region of 3×3 pixels). In this case, as shown in FIG. 26, the twenty pieces of 3×3 pixel regions have different black and white patterns. These black and white patterns can be regarded as image patterns unique to the twenty pixels (code sequences each having a length $N_L$=9; position information), respectively, and are equivalent to that the respective pixels of the images are coded by the tag patterns.

Figures 27A, 27B:
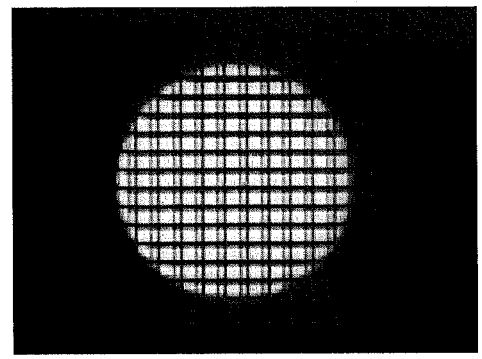
FIG. 27 is a diagram illustrating another example in which the modification is extended two-dimensionally.
Figure 28:
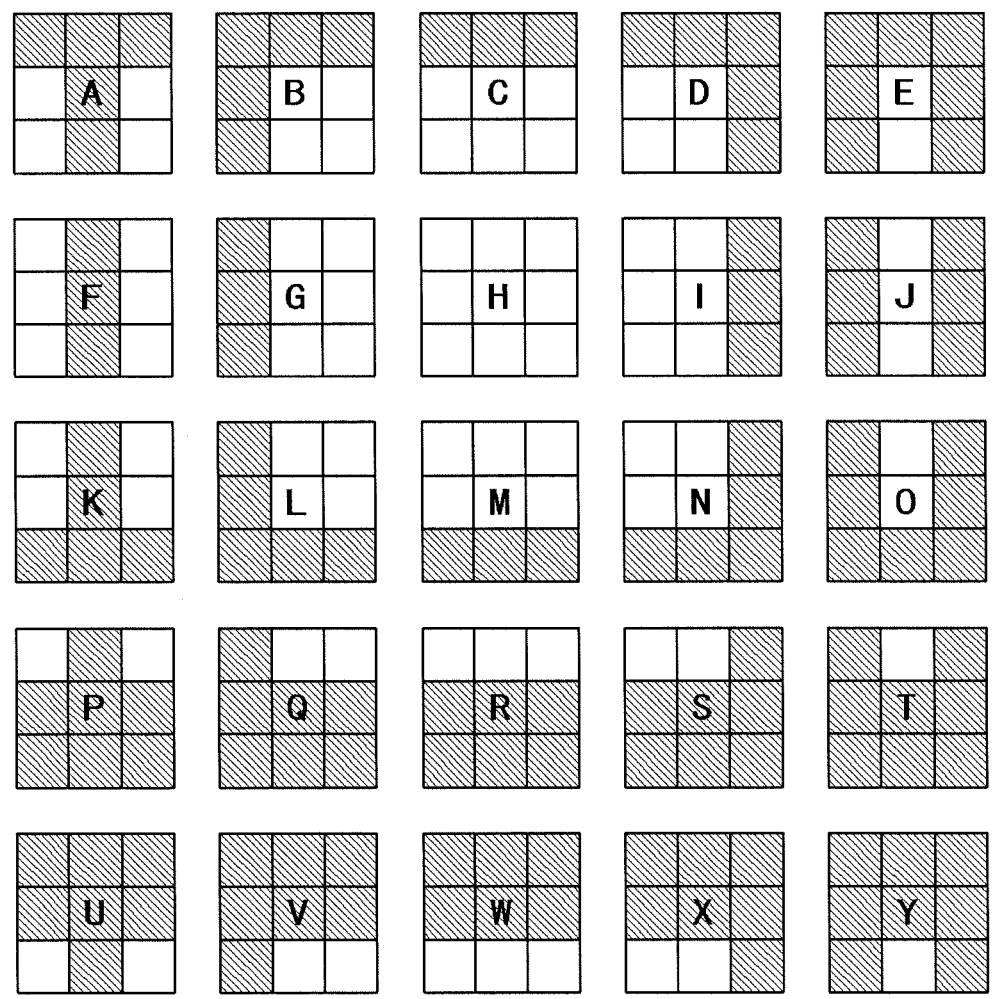
FIG. 28 is a diagram illustrating a list of image patterns each constituting a code sequence in the example of FIG. 27.
Figure 29A:
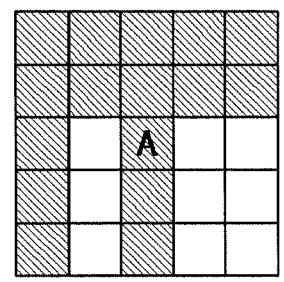
FIG. 29 is a diagram illustrating image patterns for distinguishing between A and A' in the example of FIG. 27.
Figure 29B:
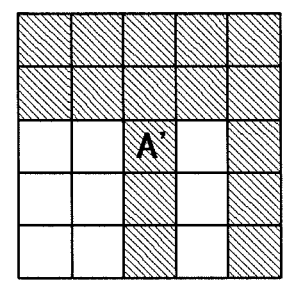

FIGS. 27 to 29 show another example in which the modification is extended to two dimensions.

A pattern shown in FIG. 27(b) also has horizontal stripes (horizontal stripe pattern) and vertical stripes (vertical stripe pattern). In the pattern shown in FIG. 27(b), when viewed in the vertical direction of the image, the ratio of the white region (white band) width to the black region (black band) width in the horizontal stripe pattern is 3:2. When viewed in the horizontal direction of the image, the ratio of the first white region width:the first black region width:the second white region width:the second black region width, in the vertical stripe pattern, is 3:1:1:1. In FIG. 27(b), hatched portions correspond to the black regions, and blank portions correspond to the white regions.

When such a tag pattern is applied to the imaging target, as shown in FIG. 27(a), a black and white pattern, in which a unit of thirty pixels (vertical 5 pixels×horizontal 6 pixels) (A to Y including A', F', K', P' and U' shown in FIG. 27(b)) is repeated in the horizontal and vertical directions, is foiiiied in a two-dimensional space as shown in FIG. 27(a), With respect to the thirty pixels A to Y, black and white patterns are considered, each pattern comprising nine pixels in which each of the pixels A to Y is located in the center (i.e., the self pixel and surrounding eight pixels; a region of 3×3 pixels). In this case, as shown in FIG. 28, twenty-five black and white patterns are obtained because the patterns for A', F', K', P' and U' are identical to the patterns for A, F, K, P and U. The twenty-five pieces of 3×3 pixel regions have different black and white patterns. These black and white patterns can be regarded as image patterns unique to the twenty-five pixels (code sequences each having a length $N_L=9$; position information), respectively, and are equivalent to that the twenty-five pixels are coded by the tag patterns.

The pixels A', F', K', P' and U' can be distinguished from the pixels A, F, K, P and U by focusing attention on pixels (e.g., the self pixel and surrounding twenty-four pixels; a region of 5×5 pixels) which surround nine pixels (e.g., the self pixel and surrounding eight pixels; a region of 3×3 pixels). All the thirty pixels may be coded for each of the 5×5 pixel regions.

It should be noted that the points not particularly described in detail in the above modifications can be executed according to the contents described with respect to FIGS. 1 to 10.

It should be noted that the matters disclosed above are merely examples. The present invention is not limited thereby, and can be changed in various ways.

For example, as a pixel signal, a phase value may be used instead of or in addition to a luminance value.

Further, motion analysis is not limited to simple detection of movement, but may be performed to obtain an elastic modulus of an imaging target from the detected amount of movement.

Further, the imaging target of the present invention is not particularly limited. However, when analysis accuracy is considered, an imaging target, such as cardiac muscle tissue, whose basic figure is maintained in spite of its movement, contraction, or expansion is preferred to an imaging target, such as a fluid like blood, which has not basis figure. That is, when blood flow is assumed, for example, there is a possibility that a portion positioned upstream in the blood flow direction might overtake a portion positioned downstream, and a continuous positional relationship of the imaging target (blood flow) at a certain time phase might be disordered in the later time phase, which makes it difficult to achieve excellent analysis accuracy. On the other hand, cardiac muscle tissue is a continuum in which a continuous positional relationship thereof in a certain time phase is maintained in spite of its motion (movement, contraction, or expansion), and therefore, is easy to analyze, which makes it easy to achieve excellent analysis accuracy.

DESCRIPTION OF THE REFERENCE CHARACTERS

1 MRI device
2 magnetic field generator
3 RF coil
4 RF transmitter
5 RF receiver
6 controller
7 A/D converter
8 computer
9 processor
10 storage unit
11 display unit

The invention claimed is:

1. A method for analyzing motion of an imaging target by means of tagged MR images, the method comprising the steps of:
    performing, on the same motion of an imaging target, $N_L$ ($N_L$: positive integer not less than 2) times of cine imaging by means of different tag patterns, to obtain $N_L$ pieces of time-series tagged MR images taken for a plurality of time phases in the motion of the imaging target;
    arranging $N_L$ pieces of pixel values of the same pixel in the $N_L$ pieces of tagged MR images at each time phase into a pixel value sequence having a length $N_L$ for the corresponding pixel; and
    analyzing the motion of the imaging target in the time-series tagged MR images by detecting pixels whose pixel value sequences constitute the same code sequence in different time phases, wherein
    each of the tag patterns is formed such that the pixel value sequence constitutes a predetermined code sequence, and wherein the step of analyzing motion of the imaging target in the time-series tagged MR images by detecting pixels includes at least calculating an amount of motion of the imaging target in a region less than the size of one pixel.

2. The motion analysis method according to claim 1, wherein in the step of analyzing motion of the imaging target, a ratio of each of a plurality of code sequences which coexist in each pixel is calculated based on the pixel value sequence.

3. The method for analyzing motion of an imaging target by means of tagged MR images according to claim 1, wherein the code sequence is an orthogonal code sequence.

4. The method for analyzing motion of an imaging target by means of tagged MR images according to claim 1, wherein the code sequence is a spread code sequence.

5. The method for analyzing motion of an imaging target by means of tagged MR images according to claim 1, wherein the code sequence is a PN sequence.

6. The method for analyzing motion of an imaging target by means of tagged MR images according to claim 1, wherein the code sequence is an M sequence.

7. A method for analyzing motion of an imaging target by means of tagged MR images, the method comprising the steps of:
    performing, on an imaging target, cine imaging by means of a predetermined tag pattern, to obtain time-series tagged MR images taken in a plurality of time phases of a motion of the imaging target;
    arranging pixel values of $N_L$ ($N_L$: positive integer not less than 2) pieces of pixels included in the tagged MR image in each time phase into a pixel value sequence having a length $N_L$ for a region comprising the $N_L$ pieces of pixels; and analyzing the motion of the imaging target in the time-series tagged MR images by detecting regions whose pixel value sequences constitute the same code sequence in different time phases, wherein the predetermined tag pattern is formed such that the pixel value sequence constitutes a predetermined code sequence, and wherein the step of analyzing motion of the imaging target in the time-series tagged MR images by detecting pixels includes at least calculating an amount of motion of the imaging target in a region less than the size of one pixel.

8. The motion analysis method according to claim 7, wherein in the step of analyzing motion of the imaging target, a ratio of a bright region or a dark region of the tag pattern within the range of each pixel is calculated based on the magnitude of the pixel value of each pixel.

9. An MRI device, comprising:

means for performing, on the same motion of an imaging target, $N_L$ ($N_L$: positive integer not less than 2) times of cine imaging by means of different tag patterns, to obtain $N_L$ pieces of time-series tagged MR images taken for a plurality of time phases in the motion of the imaging target; and means for, with a pixel value sequence comprising $N_L$ pieces of pixel values of the same pixel in the $N_L$ pieces of tagged MR images at a specific time phase being regarded as a code sequence having a length $N_L$ which indicates the corresponding pixel in the specific time phase, analyzing the motion of the imaging target in the time-series tagged MR images by detecting a pixel having a pixel value sequence to be the same code sequence as the code sequence, from the $N_L$ pieces of tagged MR images in time phases other than the specific time phase, wherein each of the tag patterns is formed such that the pixel value sequence constitutes a predetermined code sequence, and wherein the means for analyzing motion of the imaging target in the time-series tagged MR images by detecting pixels includes at least calculating an amount of motion of the imaging target in a region less than the size of one pixel.

10. The MRI device according to claim 9, wherein the means for analyzing motion of the imaging target calculates, based on the pixel value sequence, a ratio of each of a plurality of code sequences which coexist in each pixel.

11. The MRI device according to claim 9, wherein the code sequence is an orthogonal code sequence.

12. The MRI device according to claim 9, wherein the code sequence is a spread code sequence.

13. The MRI device according to claim 9, wherein the code sequence is a PN sequence.

14. The MRI device according to claim 9, wherein the code sequence is an M sequence.

15. An MRI device, comprising:

means for performing, on an imaging target, cine imaging by means of a predetermined tag pattern, to obtain time-series tagged MR images taken in a plurality of time phases of a motion of the imaging target; and means for, with a pixel value sequence comprising pixel values of $N_L$ ($N_L$: positive integer not less than 2) pieces of pixels included in the tagged MR image in a specific time phase being regarded as a code sequence having a length $N_L$ which represents a region comprising the $N_L$ pieces of pixels, analyzing the motion of the imaging target in the time-series tagged MR images by detecting a region having a pixel value sequence to be the same code sequence as the code sequence, from the tagged MR images in time phases other than the specific time phase, wherein the predetermined tag patterns is formed such that the pixel value sequence constitutes a predetermined code sequence, and wherein the means for analyzing motion of the imaging target in the time-series tagged MR images by detecting pixels includes at least calculating an amount of motion of the imaging target in a region less than the size of one pixel.

16. The MRI device according to claim 15, wherein the means for analyzing motion of the imaging target calculates, based on the magnitude of the pixel value of each pixel, a ratio of a bright region or a dark region of the tag pattern within the range of each pixel.

* * * * *